United States Patent [19]
Arai et al.

[11] Patent Number: 5,334,611
[45] Date of Patent: Aug. 2, 1994

[54] 6-ETHYL MITOMYCIN DERIVATIVES

[75] Inventors: Hitoshi Arai, Sunto; Yutaka Kanda, Machida; Motomichi Kono, Sunto; Masaji Kasai, Fujisawa; Tadashi Ashizawa, Numazu; Katsushige Gomi, Susono, all of Japan

[73] Assignee: Kyowa Hakko Kogyo Co., Ltd., Tokyo, Japan

[21] Appl. No.: 101,029

[22] Filed: Aug. 3, 1993

Related U.S. Application Data

[62] Division of Ser. No. 857,427, Mar. 26, 1992, Pat. No. 5,256,685.

Foreign Application Priority Data

Mar. 26, 1991 [JP] Japan .................................. 3-061838

[51] Int. Cl.⁵ .................... C07D 487/22; A61K 31/40
[52] U.S. Cl. ..................................... 514/410; 548/422
[58] Field of Search ........................ 548/422; 514/410

[56] References Cited

U.S. PATENT DOCUMENTS

| | | | |
|---|---|---|---|
| 4,374,774 | 2/1983 | Kasai et al. | 548/422 |
| 4,880,825 | 11/1989 | Kasai et al. | 548/422 |
| 5,068,349 | 11/1991 | Kanda et al. | 548/418 |

FOREIGN PATENT DOCUMENTS

| | | |
|---|---|---|
| 307179 | 3/1989 | European Pat. Off. . |
| 359480 | 3/1990 | European Pat. Off. . |
| 59365 | 5/1975 | Japan . |
| 1003092 | 9/1965 | United Kingdom . |

OTHER PUBLICATIONS

Chemical Abstracts, vol. 83, No. 21, Nov. 24, 1975, Columbus, Ohio, US; Abstract No. 179026b, Y. Fujimoto et al., "Mitomycin derivatives".
Abstract No. 179026b—Chemical abstracts, vol. 83, No. 21, Nov. 24, 1975, Columbus, Ohio, US; Y. Fujimoto et al., "Mitomycin derivatives" * abstract*.

*Primary Examiner*—Joseph Paul Brust
*Assistant Examiner*—MarySusan H. Gabilan
*Attorney, Agent, or Firm*—Cushman, Darby & Cushman

[57] ABSTRACT

Novel mitomycin derivatives represented by the formula (I) are obtained by introducing a substituent at the 6-position. The mitomycin derivatives of the present invention have an antitumor activity.

2 Claims, No Drawings

6-ETHYL MITOMYCIN DERIVATIVES

This is a continuation of application Ser. No. 07/857,427, filed Mar. 26, 1992, now U.S. Pat. No. 5,256,685.

FIELD OF THE INVENTION

The present invention relates to novel mitomycin derivatives having an antitumor activity.

BACKGROUND OF THE INVENTION

As mitomycin derivatives relevant to the present invention where a substituent is introduced in the methyl group at the 6-position, there are known mitomycin derivatives where one hydrogen atom of the methyl group is substituted with deuterium ($^2$H) or tritium ($^3$H) (Japanese Published Unexamined Patent Application (hereafter referred as JP-A) 70490/89) and mitomycin derivatives where one hydrogen atom of the methyl group is substituted with RO or RS (wherein R represents hydrogen, a substituted or unsubstituted alkyl having 1 to 12 carbon atoms, a substituted or unsubstituted alkenyl having 2 to 12 carbon atoms, a substituted or unsubstituted aralkyl or a substituted or unsubstituted aryl) (JP-A 167282/90).

SUMMARY OF THE INVENTION

It is the object of the present invention to provide novel mitomycin derivatives having a substituent in the methyl group at the 6-position.

The present invention relates to mitomycin derivatives represented by formula (I):

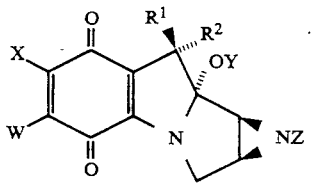
(I)

wherein W represents a substituted or unsubstituted alkyl having 2 to 19 carbon atoms, a substituted or unsubstituted cycloalkylalkyl, a substituted or unsubstituted alkenyl, a substituted or unsubstituted cycloalkenylalkyl or a substituted or unsubstituted aralkyl; X represents methoxy or amino or, X and W together form —W—X— shown by the formula:

$$-CH_2-\underset{\underset{CO_2CH_2CH_3}{|}}{\overset{\overset{CH_3}{|}}{C}}-CO-NH-$$

or

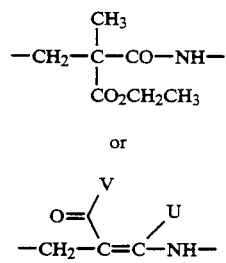

wherein U and V independently represent a substituted or unsubstituted lower alkyl, lower alkenyl or lower alkoxy group, a substituted or unsubstituted aryl or lower alkenyloxy group, or U and V together form —(CH$_2$)$_m$—CR$^3$R$^4$—CH$_2$— (wherein m represents an integer of 0 to 1 ; R$^3$ and R$^4$ independently represent hydrogen, a lower alkyl or a substituted or unsubstituted aryl); Y represents hydrogen or methyl; Z represents hydrogen, methyl, a lower alkanoyl or an allyloxycarbonyl; one of R$^1$ and R$^2$ represents carbamoyloxymethyl and the other represents hydrogen, or R$^1$ and R$^2$ together form methylene (=CH$_2$).

DETAILED DESCRIPTION OF THE INVENTION

The compound represented by the formula (I) is referred to herein as Compound (I); and the same shall apply to other compounds having a formula number.

In the definitions of the respective groups in the formula (I), the alkyl is used to mean a straight or branched alkyl group having 2 to 19 carbon atoms and the examples of the alkyl include ethyl, propyl, isopropyl, butyl, isobutyl, tert-butyl, pentyl, hexyl, heptyl, octyl, nonyl, decyl, undecyl, dodecyl, octadecyl, nonadecyl, etc.

The cycloalkylalkyl refers to a cycloalkyl group having 4 to 10 carbon atoms and the examples are cyclopropylmethyl, cyclopentylmethyl, cyclohexylmethyl, etc. The alkenyl refers to a straight or branched alkenyl group having 3 to 19 carbon atoms and the examples are allyl, butenyl, isobutenyl, pentenyl, hexenyl, heptenyl, octenyl, nonenyl, decenyl, undecenyl, dodecenyl, octadecenyl, nonadecenyl, etc.

The cycloalkenylalkyl refers to a cycloalkenylalkyl group having 4 to 10 carbon atoms and the examples are cyclopentenylmethyl, cyclohexenylmethyl, etc. Examples of the aralkyl include benzyl, phenethyl, benzhydryl, etc. Examples of the aryl include phenyl, naphthyl, etc. The lower alkanoyl refers to a lower alkanoyl group having 1 to 5 carbon atoms and the examples are formyl, acetyl, propionyl, butyryl, isobutyryl, pivaloyl, valeryl, isovaleryl, etc. The lower alkyl is used to mean a straight or branched alkyl group having 1 to 5 carbon atoms such as methyl, ethyl, propyl, isopropyl, butyl, isobutyl, tert-butyl, pentyl, etc. The lower alkoxy is used to mean a straight or branched alkoxy group having 1 to 5 carbon atoms and the examples are methoxy, ethoxy, propoxy, isopropoxy, butoxy, isobutoxy, tert-butoxy, pentyloxy, etc. The alkenyl moiety in the lower alkenyl and lower alkenyloxy refer to a straight or branched alkenyl group having 2 to 5 carbon atoms and the examples are propenyl, butenyl, isobutenyl, pentenyl, etc.

In the definitions of the respective groups in the formula (I), one or two substituents on the respective groups may be the same or different, and are, for example, lower alkoxy, lower alkanoyl, alkoxycarbonyl, aroyl, oxo, halogen, alkanoylamino, nitro, etc.

The lower alkoxy is as defined for the lower alkoxy described above. The alkanoyl refers to an alkanoyl group having 1 to 5 carbon atoms and the examples are formyl, acetyl, propionyl, butyryl, valeryl, etc. The alkoxycarbonyl refers to an alkoxycarbonyl group having 2 to 5 carbon atoms and the examples are methoxycarbonyl, ethoxycarbonyl, propoxycarbonyl, tert-butoxycarbonyl, etc. As the aroyl, there are benzoyl, p-nitrobenzoyl, naphthoyl, etc. Examples of the halogen include fluorine, chlorine, bromine, etc. The alkanoylamino refers to an alkanoylamino group having 2 to 5 carbon atoms and the examples are acetylamino, propionylamino, etc.

Processes for preparing Compound (I) are described below.

Process 1

Compound (I) can be prepared following the steps given below.

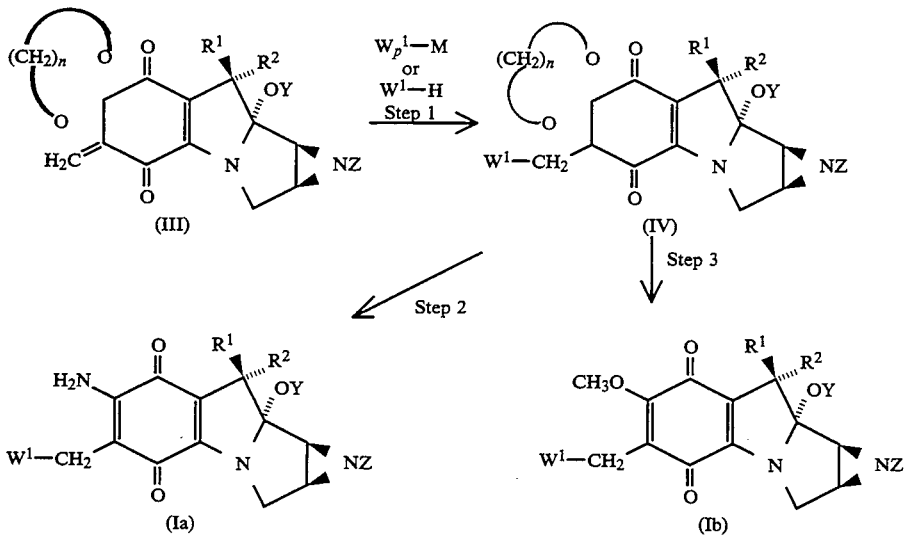

wherein n represents an integer of 2 or 3; p represents an integer of 1 or 2; Y, Z, $R^1$ and $R^2$ are as defined above; $W^1$ is a group shown by $W^1-CH_2=W$ according to the definition of W described above; and M represents a metal atom or a magnesium halide.

The metal atom described above represents sodium, lithium, copper, etc. and examples of the halogen in magnesium halide are chlorine, bromine, iodine, etc.

Step 1

Compound (IV) can be obtained by reacting Compound (III) with a compound of the formula $W^1$ p—M (wherein $W^1$, M and p are as defined above). The reaction may also be carried out in the presence of a monovalent copper catalyst, depending upon the property of the compound $W^1$ p—M. Examples of the monovalent copper catalyst are copper (I) iodide, etc. The suitable amount of the catalyst is in the range of 0.01 to 1.0 equivalent, preferably 0.05 to 0.3 equivalent, based on Compound (III).

Compound (IV) may also be obtained by reacting Compound (III) with a compound of the formula $W^1$—H (wherein $W^1$ is as defined above) in the presence of a base. As the base, mention may be made of alcoholates, hydroxides, carbonates or hydrogencarbonate of alkali metals or alkaline earth metals, tertiary amines or quaternary ammonium hydroxides, etc. The base may be used in an amount of at least 1 equivalent based on Compound (III).

These processes may be suitably applied depending upon the property of $W^1$. As the reaction solvent, there are, for example, ethers such as diethyl ether, tetrahydrofuran, etc.; halogenated alkane solvents such as dichloromethane, chloroform, etc.; acetonitrile, dimethylformamide (DMF), dimethylsulfoxide, etc. The solvent may be chosen depending upon reactants and used singly or as admixture. The reaction is carried out generally at −78° to 30° C. and completed in 1 minute to 24 hours.

The starting Compound (III) is a known compound described in JP-A 70490/89.

Step 2

Compound (Ia) [in the formula (I), X represents $NH_2$] can be obtained by reacting Compound (IV) with ammonia or ammonium acetate.

Any reaction solvent may be used so long as it is inert to the reaction and can dissolve Compound (IV). As the reaction solvent, there may be used, for example, alcohol type solvents such as methanol, ethanol, etc.; ether type solvents such as diethyl ether, tetrahydrofuran, etc.; halogenated alkane type solvents such as dichloromethane, chloroform, etc.; acetonitrile, DMF, dimethylsulfoxide, etc., singly or in combination. The reaction is carried out generally at 0° to 30° C. and completed in an hour to 14 days.

Step 3

Compound (Ib) [in the formula (I), X represents $CH_3O$] can be obtained by reacting Compound (IV) in the presence of a base or silica gel in methanol.

As the base, there may be used alcoholates, hydroxides, carbonates or hydrogencarbonates of alkali metals or alkaline earth metal, tertiary amines or quaternary ammonium hydroxides, etc. The base may be used in an amount of 0.001 to 10 equivalents, preferably 0.01 to 3 equivalents, based on Compound (IV). The reaction is carried out generally at 0° to 30° C. and completed in 1 to 24 hours.

As the silica gel, there may be used in an excess amount based on Compound (IV). The reaction is carried out generally 40° C. to the boiling point of the solvent and completed in 1 to 24 hours.

In Steps 2 and 3, deacylation simultaneously occurs in Compound (IV), wherein Z represents a lower alkanoyl, under the reaction conditions described above to give the corresponding Compound (Ia) and Compound (Ib) wherein Z is a hydrogen atom, respectively.

Process 2

Compound (I) may also be prepared following the steps given below.

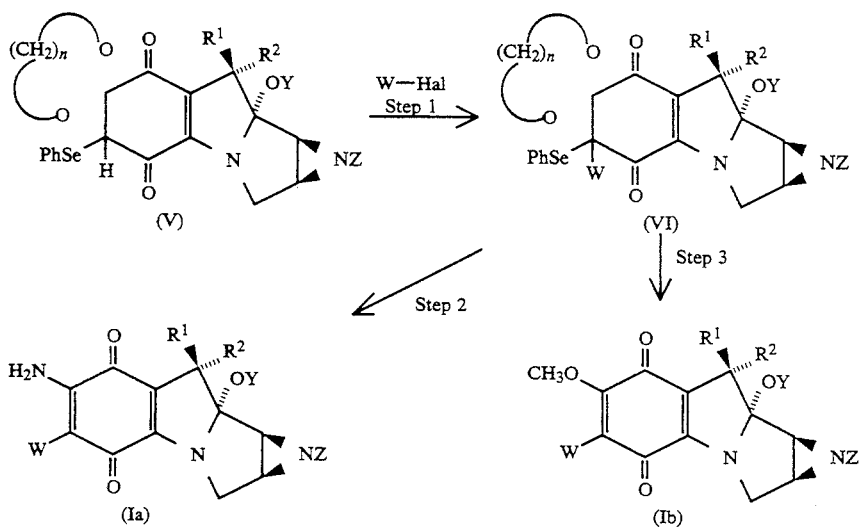

wherein n, W, Y, Z, $R^1$ and $R^2$ are as defined above; Ph represents phenyl; and Hal represents a halogen atom. The halogen atom described above refers to chlorine, bromine, iodine, etc.

Step 1

Compound (VI) can be obtained by reacting Compound (V) with a compound of the formula W-Hal (wherein Hal and W are as defined above) in the presence of a base in an inert solvent.

Examples of the reaction solvent are acetone, acetonitrile, dimethyl ether, tetrahydrofuran, dichloromethane, chloroform, DMF, etc. These solvents may be used singly or as admixture. As the base, mention may be made of carbonates, hydrogencarbonates or hydroxides of alkali metals such as cesium carbonate, potassium carbonate, sodium carbonate, etc., tertiary amines such as triethylamine, pyridine, etc. or quaternary ammonium hydroxides, etc. The base may be used generally in an excess amount, preferably in 1.5 to 10 equivalents, based on Compound (V). The reaction may be carried out generally at 0° to 30° C. and completed in an hour to 7 days.

The starting Compound (V) is a known compound described in JP-A 14582/91.

Step 2

Compound (Ia) can be obtained by reacting Compound (VI) with ammonia in the presence of dimedone in a solvent.

As the solvent, the same solvent as in Step 2 of Process 1 may be used. Dimedone may be used in an excess amount, preferably 2 to 5 equivalents based on Compound (VI). The reaction is carried out generally at 0° to 30° C. and completed in an hour to 14 days.

Step 3

Compound (Ib) can be obtained by reacting Compound (VI) in methanol in the presence of a base and dimedone.

The same solvent and base as used in Step 3 of Process 1 may be used. Dimedone may be used in an excess amount, preferably 2 to 5 equivalents based on Compound (V). The amount of the base is used in an excess amount, preferably in the range of 1.01 to 4 equivalents, based on dimedone, and may be varied depending upon a type of the base used. The reaction is carried out generally at 0° C. to 30° C. and completed in 1 to 24 hours.

In Steps 2 and 3, deacylation occurs simultaneously in Compound (VI), wherein Z represents a lower alkanoyl, under the reaction conditions with dimedone described above to give the corresponding Compound (Ia) and Compound (Ib) wherein Z is a hydrogen atom, respectively.

Process 3

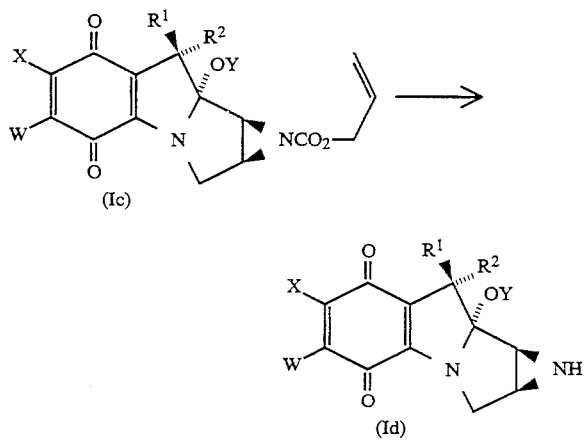

wherein W, X, Y, $R^1$ and $R^2$ are as defined above.

Compound (I) wherein Z is hydrogen, i.e. Compound (Id), can be obtained by reacting Compound (Ic) wherein Z is an allyloxycarbonyl, with a suitable reducing agent in the presence of a palladium catalyst in a solvent inert to the reaction.

The palladium catalyst is a catalyst which forms a zero valency homogeneous active species and there are used, for example, tetrakis (triphenylphosphine) palladium (0) or palladium (II) acetate in the presence of triphenylphosphine. The amount of the catalyst added is 0.01 to 1.0 equivalent, preferably 0.1 to 0.5 equivalent based on Compound (Ic). As the reducing agent, formic acid, triethylammonium formate, tributyltin hydride, triphenyltin hydride, trimethylhydrosilane, sodium borohydride and the like may be used in an excess amount, based on Compound (Ic). As the solvent, diethyl ether, tetrahydrofuran, acetonitrile, DMF and the like may be used singly or as admixture. The reaction is carried out at −20° to 80° C., preferably 0° to 30° C. and completed in 10 minutes to 10 hours.

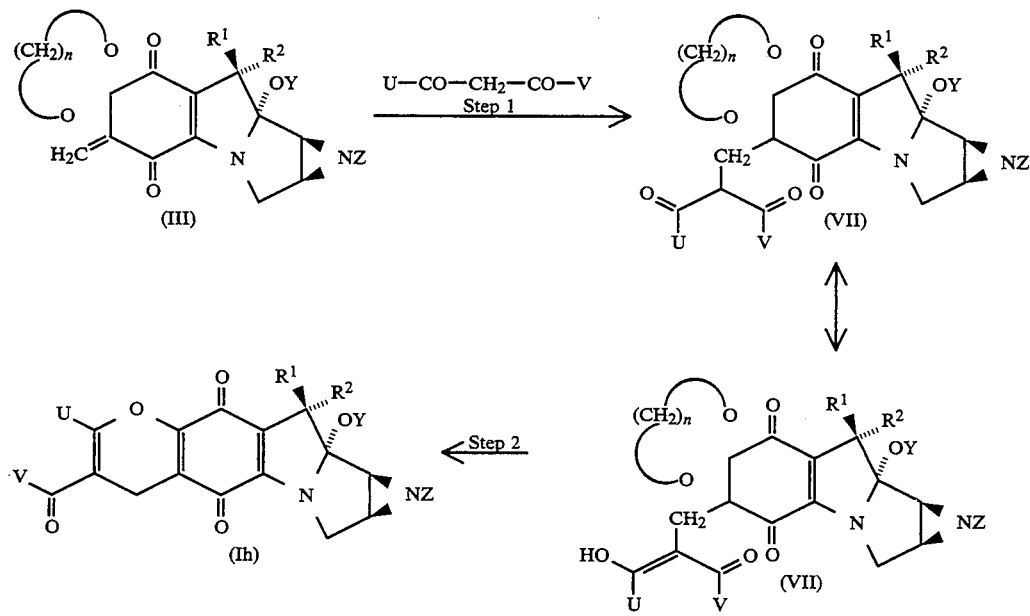

Process 5

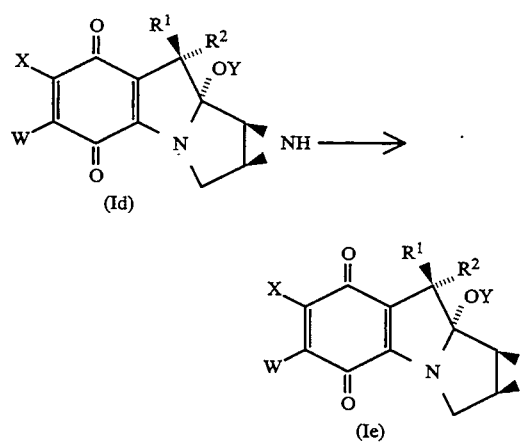

Process 4 wherein W, X, Y, $R^1$ and $R^2$ are as defined above.

Compound (I) wherein Z is methyl, i.e. Compound (Ie), can be obtained by reacting Compound (Id), Compound (I) wherein Z is hydrogen, with methyl iodide in the presence of a base in a solvent inert to the reaction.

The same solvent and base as used in Step 1 of Process 2 may be used. The reaction is carried out generally at 0° to 120° C. preferably 20° to 60° C. and completed in 1 to 30 hours. Compound (I) wherein X and W are combined together, i.e. Compound (Ih) represented by the formula:

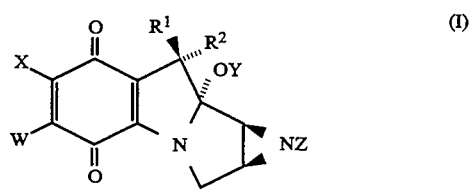

wherein $R^1$, $R^2$, Y, Z, U and V are as defined above, can be obtained by the process shown below.

Step 1

Compound (VII) can be obtained by reacting Compound (III) and the salt obtained by treating U—CO—CH$_2$—CO—V (wherein U and V are as defined above) with a base in a solvent inert to the reaction. Depending upon a type of U—CO—CH$_2$—CO—V used, Compound (Ih) may further be obtained.

Compound (VII) may also be obtained by reacting Compound (III) with U—CO—CH$_2$—CO—V (wherein U and V are as defined above) in the presence of a base in a solvent inert to the reaction.

Examples of the solvent used in the reaction are ether type solvents such as diethyl ether, tetrahydrofuran, etc.; halogenated alkane type solvents such as dichloromethane, chloroform, etc.; acetonitrile, DMF, dimethylsulfoxide, etc. The suitable solvent may be chosen depending upon the properties of reactants and used singly or as admixture. As the base, there may be used hydrides, alcoholate, carbonates or hydrogencarbonates of alkali metals or alkaline earth metals; tertiary amines or quaternary ammonium hydroxides. The base may be used in an amount of 1 equivalent or more. The reaction is carried out generally at −78° to 30° C. and completed in a minute to 24 hours.

Step 2

Compound (Ih) can be obtained by dissolving Compound (VII) in a solvent, adsorbing onto silica gel and allowing to stand.

As the solvent, mention may be made of halogenated alkane solvents such as dichloromethane, chloroform, etc. The reaction is carried out generally at 0° to 40° C. and completed in an hour to 7 days.

Process 6

Compound (Ih) wherein Z is hydrogen i.e. Compound (Iha), can also be obtained by reacting Compound (Ihc) where Z is a lower alkanoyl, in the presence of a base in methanol.

Examples of the base which can be used in the reaction are ammonia, alcoholates, hydroxides, carbonates or hydrogencarbonates of alkali metals or alkaline earth metals; tertiary amines or quaternary ammonium hydroxides. The base is used in a catalytic amount or in an excess amount based on Compound (Ihc), depending upon a type of the base. The reaction is carried out at 0° to 30° C. and completed in 1 to 24 hours.

Process 7

Compound (Ih) wherein Z is hydrogen, i.e. Compound (Iha), can be prepared by reacting Compound (Ihd) wherein Z is an allyloxycarbonyl, with a suitable reducing agent in the presence of a palladium catalyst in a solvent inert to the reaction.

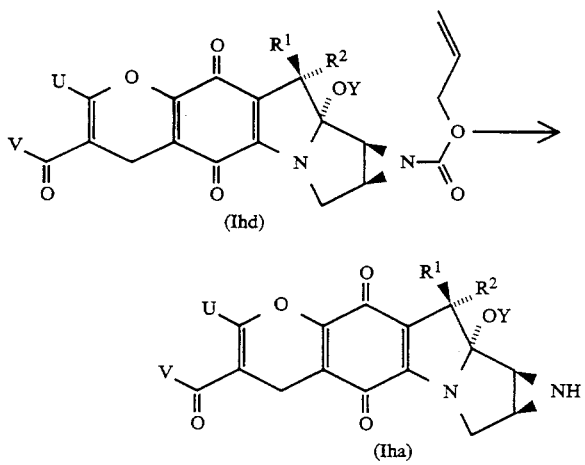

wherein U, V, Y, $R^1$ and $R^2$ are defined above.

The palladium catalyst used is a catalyst that forms a zero valency homogeneous active species and there are used, for example, tetrakis (triphenylphosphine)palladium (0) or palladium (II) acetate in the presence of triphenylphosphine. The amount of the catalyst added is 0.01 to 1.0 equivalent, preferably 0.1 to 0.5 equivalent based on Compound (Ihd).

As the reducing agent, formic acid, triethylammonium formate, tributyltin hydride, triphenyltin hydride, trimethylhydrosilane and the like may be used in an excess amount, based on Compound (Ihd).

As the solvent, diethyl ether, tetrahydrofuran, acetonitrile, DMF and the like may be used singly or as admixture.

The reaction is carried out at −20° to 80° C., preferably 0° to 30° C. and completed in 10 minutes to 10 hours.

The intermediates and the desired products in the process described above may be isolated and purified by purification techniques conventionally used in organic synthetic chemistry, for example, neutralization, filtration, extraction, washing, drying, concentration, recrystallization, various chromatographies, etc. In the case of the intermediates, they can be applied directly to the subsequent step without any further purification. Furthermore, Compounds (I) may be obtained in the form of addition products with water or various solvents, which are also within the scope of the present invention.

Specific examples of Compounds (I) obtained by the processes described above are shown in Tables 1 and 2.

TABLE 1

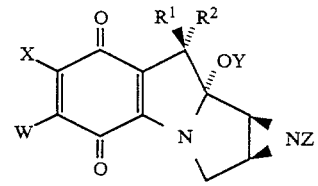

| Compound | (Example No.) | W | X | Y | Z | $R^1$ | $R^2$ |
|---|---|---|---|---|---|---|---|
| 1 | (1) | $CH_2CH_3$ | $NH_2$ | $CH_3$ | H | $CH_2OCONH_2$ | H |
| 2 | (2) | $CH_2CH_3$ | $NH_2$ | $CH_3$ | $CH_3$ | $CH_2OCONH_2$ | H |
| 3 | (3) | $CH_2CH_3$ | $NH_2$ | H | $CH_3$ | H | $CH_2OCONH_2$ |
| 4 | (4) | $(CH_2)_2CH_3$ | $NH_2$ | $CH_3$ | H | $CH_2OCONH_2$ | H |
| 5 | (5) | $CH_2CH=CH_2$ | $NH_2$ | $CH_3$ | H | $CH_2OCONH_2$ | H |
| 6 | (6) | $(CH_2)_4CH_3$ | $NH_2$ | $CH_3$ | H | $CH_2OCONH_2$ | H |
| 7 | (7) | $CH_2Ph$ | $NH_2$ | $CH_3$ | H | $CH_2OCONH_2$ | H |
| 8 | (8) | $(CH_2)_2NO_2$ | $NH_2$ | $CH_3$ | H | $CH_2OCONH_2$ | H |
| 9 | (9) | ![cyclohexenone-CH2 substituent] | $NH_2$ | $CH_3$ | H | $CH_2OCONH_2$ | H |
| 10 | (10) | $CH_2-\underset{CH_3}{\underset{|}{\overset{COCH_3}{\overset{|}{C}}}}-CO_2CH_2CH_3$ | $OCH_3$ | $CH_3$ | H | $CH_2OCONH_2$ | H |

TABLE 1-continued

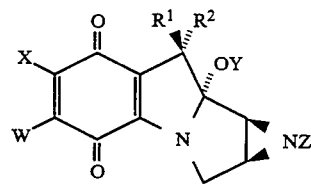

| Compound | (Example No.) | W | X | Y | Z | R[1] | R[2] |
|---|---|---|---|---|---|---|---|
| 11 | (11) | $CH_2-\underset{\underset{CO_2CH_2CH_3}{\|}}{\overset{\overset{CH_3}{\|}}{C}}-CONH$ | | $CH_3$ | H | $CH_2OCONH_2$ | H |
| 15 | (15) | $CH_2CH_3$ | $OCH_3$ | $CH_3$ | H | $CH_2OCONH_2$ | H |
| 16 | (16) | $CH_2CH_3$ | $OCH_3$ | H | $CH_3$ | H | $CH_2OCONH_2$ |
| 17 | (17) | $CH_2CH(CH_3)_2$ | $NH_2$ | $CH_3$ | H | $CH_2OCONH_2$ | H |
| 18 | (18) | $CH_2CH(CH_3)_2$ | $OCH_3$ | $CH_3$ | H | $CH_2OCONH_2$ | H |
| 19 | (19) | $CH_2CH(CH_3)_2$ | $OCH_3$ | H | $CH_3$ | H | $CH_2OCONH_2$ |
| 20 | (20) | $(CH_2)_4CH_3$ | $OCH_3$ | $CH_3$ | H | $CH_2OCONH_2$ | H |
| 21 | (21) | $(CH_2)_4CH_3$ | $OCH_3$ | H | $CH_3$ | H | $CH_2OCONH_2$ |
| 22 | (22) | $CH_2Ph$ | $OCH_3$ | $CH_3$ | H | $CH_2OCONH_2$ | H |
| 23 | (23) | $CH_2Ph$ | $OCH_3$ | H | $CH_3$ | H | $CH_2OCONH_2$ |
| 24 | (24) | $(CH_2)_{10}CH_3$ | $NH_2$ | $CH_3$ | H | $CH_2OCONH_2$ | H |
| 25 | (25) | $(CH_2)_{10}CH_3$ | $OCH_3$ | $CH_3$ | H | $CH_2OCONH_2$ | H |
| 26 | (26) | $(CH_2)_{18}CH_3$ | $NH_2$ | $CH_3$ | H | $CH_2OCONH_2$ | H |
| 27 | (27) | $(CH_2)_{18}CH_3$ | $OCH_3$ | $CH_3$ | H | $CH_2OCONH_2$ | H |
| 28 | (28) | $CH_2-\underset{H}{\overset{\overset{CO-\text{C}_6H_4-NO_2}{\|}}{C}}-CO_2CH_2CH_3$ | $OCH_3$ | $CH_3$ | $CH_3$ | $CH_2OCONH_2$ | H |

TABLE 2

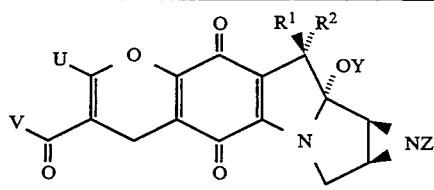

| Compound | (Example No.) | U | V | Y | Z | R[1] | R[2] |
|---|---|---|---|---|---|---|---|
| 12 | (12) | $CH_3$ | $OCH_2CH_3$ | $CH_3$ | H | $CH_2OCONH_2$ | H |
| 13 | (13) | $CH_2C(CH_3)_2CH_2$ | | $CH_3$ | H | $CH_2OCONH_2$ | H |
| 14 | (14) | $(CH_2)_3$ | | $CH_3$ | H | $CH_2OCONH_2$ | H |
| 29 | (29) | $CH_3$ | $CH_3$ | $CH_3$ | $CH_3$ | $CH_2OCONH_2$ | H |
| 30 | (30) | Ph | $CH_3$ | $CH_3$ | H | $CH_2OCONH_2$ | H |
| 31 | (31) | Ph | $CH_3$ | $CH_3$ | $CH_3$ | $CH_2OCONH_2$ | H |
| 32 | (32) | $CH_3$ | $OCH_2CH_3$ | $CH_3$ | $CH_3$ | $CH_2OCONH_2$ | H |
| 33 | (28) | $p-NO_2Ph$ | $OCH_2CH_3$ | $CH_3$ | $CH_3$ | $CH_2OCONH_2$ | H |
| 34 | (33) | $CH_2C(CH_3)_2CH_2$ | | H | $CH_3$ | H | $CH_2OCONH_2$ |
| 35 | (34) | $(CH_2)_3$ | | H | $CH_3$ | H | $CH_2OCONH_2$ |
| 36 | (35) | $CH_2CH(CH_3)CH_2$ | | $CH_3$ | H | $CH_2OCONH_2$ | H |
| 37 | (35) | $CH_2CH(CH_3)CH_2*^1$ | | $CH_3$ | H | $CH_2OCONH_2$ | H |
| 38 | (36) | $CH_2CH(p-CH_3OPh)CH_2$ | | $CH_3$ | H | $CH_2OCONH_2$ | H |
| 39 | (36) | $CH_2CH(p-CH_3OPh)CH_2*^2$ | | $CH_3$ | H | $CH_2OCONH_2$ | H |
| 40 | (37) | $CH_2-\underset{H}{\overset{\overset{2,6-Cl_2C_6H_3}{\|}}{C}}-CH_2$ | | $CH_3$ | H | $CH_2OCONH_2$ | H |

*[1]Diastereomer of Compound 36
*[2]Diastereomer of Compound 38

In the following, the antitumor activity of representative Compound (I) is specifically shown with reference to the experiments.

Experiment 1

Growth inhibition test on HeLaS3 cells:

HeLaS3 cells were suspended in an MEM medium containing 10% fetal calf serum and 2 mM glutamine at a density of $3 \times 10^4$ cells/ml, and 0.1 ml of the cell suspension was put into each well of a 96-well microtiter plate.

After culturing at 37° C. overnight in a carbon dioxide gas incubator, 0.05 ml each of a test compound appropriately diluted with the medium was added to each well. The cells were further cultured for an hour in the carbon dioxide gas incubator, and the culture supernatant was removed. The residue was washed once with a phosphate buffered saline [PBS (−)] and 0.1 ml each of a fresh medium was added to each well. The cells were further incubated at 37° C. for 72 hours in the carbon dioxide gas incubator. After removal of the culture supernatant, 0.1 ml each of the culture medium containing 0.02% Neutral Red was added to each well, and the cells were further incubated at 37° C. for an hour in the carbon dioxide gas incubator to stain the cells.

After removal of the culture supernatant, each well was washed once with a physiological saline, and the dye was extracted with 0.001 N HCl/30% ethanol. Absorbance of the extract at 550 nm was measured with a microplate reader. The cell growth inhibition percentage was calculated according to the following equation from the absorbance of the extract of the cells treated with the test compound in various concentrations and that of the untreated cells.

Cell Growth Inhibition Percentage (%) =

$$100 - \frac{\text{(Absorbance of cells treated with test compound)} - \text{(Absorbance of cell-free well)}}{\text{(Absorbance of intact cells)} - \text{(Absorbance of cell-free well)}} \times 100$$

From the cell growth inhibition percentage thus obtained, the concentration of the test compound which inhibits cell growth by 50%, i.e. IC$_{50}$ value, was determined.

The results are shown in Table 3.

TABLE 3

| Compound | IC50(mM) |
|---|---|
| 1 | 3.0 |
| 7 | 2.3 |
| 9 | 1.5 |
| 10 | 1.6 |
| 13 | 0.084 |
| 14 | 0.065 |
| 15 | 0.017 |
| 16 | 0.30 |
| 18 | 0.20 |
| 20 | 0.087 |
| 22 | 0.063 |
| 23 | 0.52 |
| 29 | 0.36 |
| 31 | 0.31 |
| 32 | 0.10 |
| 36 | 0.093 |
| 37 | 0.076 |
| 38 | 0.14 |
| 39 | 0.43 |
| 40 | 0.53 |

Experiment 2

Anti-tumor activity to sarcoma 180 solid tumor:

$5 \times 10^6$ Sarcoma 180 cells were abdominally implanted into a ddY mouse and the cells were collected from the ascites of the mouse 7 days after the implantation. The cells were washed once with a sterilized physiological saline solution and then suspended in a sterilized physiological saline solution to prepare a cell suspension of $5 \times 10^7$ cells/ml.

0.1 ml of the cell suspension was subcutaneously implanted into the right axillary space of male ddY mice weighing 20±2 g.

A test compound was dissolved in a physiological saline solution or a polyoxyethylene sorbitan monolaurate-containing physiological saline solution, and 0.1 to 0.2 ml of the solution was intravenously injected to 5 mice as one group 24 hours after the implantation of the tumor cells.

The anti-tumor activity of the test compound was determined by measuring the major axis (a) and the minor axis (b) of the tumor 7 days after the implantation of tumor cells, and the value of $(a \times b^2/2)$, which corresponds to the volume of the tumor, was calculated. The intended anti-tumor activity is represented by a ratio of T/C, in which C indicates the tumor volume of mice of the control group to which no test compound was administered and T indicates the tumor volume of mice of the test group to which the test compound was administered. T/C at each dose given was plotted on the vertical axis and a dose is shown by a logarithmic scale on the horizontal axis. The relationship between the dose and T/C was determined to be a straight line by the least squares method. From the regression formula of the straight line thus obtained, the dose showing T/C=0.5 was calculated to give ED$_{50}$.

TABLE 4

| Compound | ED50(mg/kg) |
|---|---|
| 1 | 6.7 |
| 7 | 18 |
| 9 | 8.0 |
| 12 | 0.70 |
| 13 | 1.3 |
| 14 | 0.84 |
| 15 | 2.8 |
| 16 | 14 |
| 30 | 5.8 |
| 36 | 1.3 |
| 37 | 0.93 |
| 38 | 12 |

Experiment 3

Acute toxicity:

A test compound was intravenously injected once to five ddY mice as one group. After the administration, the mice were observed for 14 days and deaths were recorded. LD$_{50}$ was calculated from the death rate of each group to which the test compound was administered according to the Behrens-Kaerber's method.

The results are shown in Table 5.

TABLE 5

| Compound | LD50(mg/kg) |
|---|---|
| 1 | 38 |
| 7 | >50 |
| 9 | 30 |
| 12 | 5.2 |
| 13 | 2.9 |
| 14 | 2.2 |

TABLE 5-continued

| Compound | LD50(mg/kg) |
|---|---|
| 15 | 8.2 |
| 16 | 25 |
| 36 | 4.4 |

The compounds obtained by the present invention are useful as anti-tumor agents, which can be used directly as such, or in various dosage forms. For example, where Compound (I) is used in the form of an injection, it may be dissolved in a diluent conventionally used in the art, such as a physiological saline, or glucose, lactose or mannitol solution for injection. Alternatively, Compound (I) may be freeze-dried according to a conventional manner to give a product for injection or may be prepared into injectable powder by adding sodium chloride thereto. In addition, the injection may also contain an auxiliary agent such as polyethylene glycol, HCO-60 (surfactant manufactured by Nikko Chemical Co., Ltd.), as well as a carrier such as ethanol and/or liposome or cyclodextrin. These injections are generally used for intravenous administration but may also be used for intra-arterial, intra-peritoneal or intra-thoracial administration.

Compound (I) may also be administered orally by mixing with an appropriate excipient, a disintegrator, a binder, a lubricant, etc. in a conventional manner to prepare a tablet, a granule, a powder or a syrup. Furthermore, Compound (I) may be mixed with a conventionally used carrier and formed into a suppository for rectum administration.

Dosage may appropriately vary depending upon the administration route, the kind of Compound (I), and the age and condition of a patient. The administration route, may also be varied according to the condition of a patient and the dosage. For example, Compound (I) can be intermittently administered in a dose of 0.06 to 6 mg/kg, once a week or once every 3 weeks.

Hereafter the present invention is described with reference to the following examples.

Physicochemical data of each compound were obtained using the following devices.

TLC: silica gel Art 5715 (manufactured by Merck Inc.)
MS: Hitachi M-80B (determined by EI or SI method) JEOL, Ltd. JMS-D300 (determined by FAB method)
IR: Nippon Bunko IR-810 (measured by the KBr method)
$^1$H-NMR: Bruker AM400 (400 MHz) JEOL, Ltd. JNM-GX270 (270 MHz) VARIAN EM390 (90 MHz)

EXAMPLES

Example 1

Synthesis of 6-demethyl-6-ethylmitomycin C
(Compound 1)

After 55.9 mg of la-acetyl-7-demethoxy-6-demethyl-7-ethylenedioxy-6, 7-dihydro-6-phenylselenomitomycin A (JP-A 70940/89) was dissolved in 1.0 ml of anhydrous acetonitrile, 100 μl of ethyl iodide and 65 mg of cesium carbonate were added to the solution. The mixture was stirred at 20° C. for 45 hours. After the reaction mixture was diluted with dichloromethane, and washed successively with a phosphate buffer (pH 4), saturated aqueous sodium hydrogencarbonate solution and saturated aqueous sodium chloride solution. The reaction mixture was then dried over anhydrous sodium sulfate. After the desiccant was removed by filtration, the solvent was distilled off to give the crude product of la-acetyl-7-demethoxy-6-demethyl-7-ethylenedioxy-6, 7-dihydro-6-ethyl-6-phenylselenomitomycin A.

The whole amount of the resulting crude product was dissolved in 2.0 ml of a 6.1M solution of ammonia in methanol and 50 mg of dimedone was added to the solution. The mixture was stirred at 20° C. for 3 hours and a half. The reaction mixture was diluted with dichloromethane and then washed successively with a phosphate buffer (pH 4), saturated aqueous sodium hydrogencarbonate solution and saturated aqueous sodium chloride solution. After the reaction mixture was dried over anhydrous sodium sulfate, the solvent was distilled off. The residue obtained was purified by preparative TLC (silica gel; chloroform:methanol=9:1) to give a violet fraction containing the desired product. This fraction was extracted with the developing solvent. After the Solvent was distilled off, the residue was dissolved in a small amount of chloroform. n-Hexane was added to the solution to give a powder. The solvent was distilled off and the residue was thoroughly dried in vacuo to give 6.0 mg (yield 17%) of Compound 1 as a violet powder.

TLC: $R_f$=0.35 (chloroform:methanol=9:1) EI-MS: m/e 348 (M+); $C_{16}H_{20}N_4O_5$=348 IR (cm$^{-1}$): 3430, 3330, 2930, 1710, 1650, 1600, 1540, 1450, 1340, 1260, 1220, 1070 $^1$H-NMR (400 MHz, pyridine-d$_5$) δ(ppm): 1.08 (t, J=7.4 Hz, 3H), 2.10 (br, 1H), 2.61 (q, J=7.4 Hz, 2H), 2.74 (dd, J=1.7 & 4.4 Hz, 1H), 3.13 (d, J=4.2 Hz, 1H), 3.21 (s, 3H), 3.61 (dd, J=1.7 & 12.6 Hz, 1H), 4.03 (dd, J=4.2 & 11.1 Hz, 1H), 4.58 (d, J=12.6 Hz, 1H), 5.08 (bt, J=11.1 Hz, 1H), 5.43 (dd, J=4.2 & 10.3 Hz, 1H), 7.60 (br, 2H), 7.67 (br, 2H)

Example 2

Synthesis of 6-demethyl-6-ethylporfiromycin
(Compound 2)

Compound 1 (50.0 mg) obtained in EXAMPLE 1 was dissolved in acetone and, 19.4 mg of potassium carbonate and 0.5 ml of methyl iodide were added to the solution. The mixture was stirred at 20° C. for 23 hours. The solvent was distilled off and the residue was purified by column chromatography (silica gel; chloroform:methanol=30:1) to give a violet fraction. From this fraction the solvent was distilled off and a small amount of chloroform was added thereto. n-Hexane was added to the mixture to give a powder. The powder was then thoroughly dried in vacuo to give 30.0 mg (yield 58%) of Compound 2 as a violet powder.

TLC: $R_f$=0.37 (chloroform:methanol=9.1) FAB-MS (m/z): 363 (M++1); $C_{17}H_{22}N_4O_5$=362 IR (cm$^{-1}$): 3430, 3320, 3200, 2950, 2870, 1720, 1600, 1570, 1550, 1450, 1340, 1210, 1110, 1070 $^1$H-NMR (270 MHz, pyridine-d$_5$) δ(ppm): 1.09 (t, J=7.4 Hz, 3H), 2.15 (dd, J=2.1 & 4.8 Hz, 1H), 2.24 (s, 3H), 2.54 (d, J=4.6 Hz, 1H), 2.63 (q, J=7.6 Hz, 2H), 3.18(s, 3H), 3.54 (dd, J=2.1 & 12.8 Hz, 1H), 4.01 (dd, J=4.2 & 11.5 Hz, 1H), 4.52 (d, J=12.9 Hz, 1H), 4.83 (dd, J=10.5 & 11.2 Hz, 1H), 5.39 (dd, J=4.3 & 10.4 Hz, 1H), 7.4–8.0 (br, 4H)

Example 3

Synthesis of 6-demethyl-6-ethylmitomycin D
(Compound 3)

After 1.19 g (purity 60%) of Compound c obtained in REFERENCE EXAMPLE 3 was dissolved in 20 ml of anhydrous tetrahydrofuran, 18 ml of a 0.25M solution of lithium dimethyl cuprate in tetrahydrofuran was added dropwise at −78° C. over 30 minutes. The mixture was stirred at −78° C. for 30 minutes. Saturated aqueous ammonium chloride solution was added to the reaction mixture. The mixture was stirred and then extracted with chloroform. The organic layer was washed with saturated aqueous sodium chloride solution, and dried over anhydrous sodium sulfate, and then the solvent was distilled off. The residue obtained was dissolved in a small amount of chloroform and n-hexane was added to the solution to give a powder. The solvent was again distilled off to give the crude product of 7-demethoxy-6-demethyl-6-ethyl-7-ethylenedioxy-6,7 -dihydromitomycin B as a brown powder.

The whole amount of the crude product obtained was dissolved in 50 ml of methanol and 10 ml of a 6.8M solution of ammonia in methanol. The solution was allowed to stand at 20° C. for 9 hours and a half. After the solvent was distilled off, the residue obtained was purified by column chromatography (silica gel; chloroform:methanol =25:1) to give a violet fraction. This fraction was treated in a conventional manner to give 76.4 mg (yield 12%) of Compound 3 as a violet powder.

TLC: $R_f=0.28$ (chloroform:methanol=9:1) EI-MS: m/z 348 (M+); $C_{16}H_{20}N_4O_5=348$ IR (cm$^{-1}$): 3420, 3330, 3270, 3200, 2950, 2870, 1710, 1700, 1600, 1560, 1550, 1540, 1450, 1420, 1350, 1060 $^1$H-NMR (90 MHz, pyridine-d$_5$) δ(ppm): 1.04 (t, J=7.5 Hz, 3H), 2.13(s, 3H), 2.23 (dd, J=1.6 & 4.8 Hz, 1H), 2.48 (d, J=4.8 Hz, 1H), 2.57(q, J=7.5 Hz, 2H), 3.69 (dd, J=1.8 & 13 Hz, 1H), 4.27 (dd, J=3.7 & 10 Hz, 1H), 4.48 (d, J=13 Hz, 1H), 5.25(t, J=10 Hz, 1H), 5.55 (dd, J=3.7 & 10 Hz, 1H), 7.3–7.6 (br, 4H), 8.23 (s, 1H)

Example 4

Synthesis of 6-demethyl-6-n-propylmitomycin C
(Compound 4)

To a solution of 430 mg of Compound a obtained in REFERENCE EXAMPLE 1 in 20 ml of anhydrous tetrahydrofuran was added 50 mg of copper (I) iodide followed by the dropwise addition of 1.0 ml of a 3.0M solution of ethylmagnesium bromide in diethyl ether at −78° C. over 20 minutes. The mixture was stirred at −78° C. for further 40 minutes. The yellow orange reaction mixture was diluted with a phosphate buffer (pH 4). After the resultant reddish pink organic layer was separated, the aqueous layer was extracted with dichloromethane. The organic layer was washed successively with saturated aqueous sodium hydrogencarbonate solution and saturated aqueous sodium chloride solution and then dried over anhydrous sodium sulfate. The solvent was then distilled off. The residue was purified by column chromatography (silica gel; chloroform:methanol=20:1) to give a yellowish pink fraction containing the desired product. This fraction was treated in a conventional manner to give 112.8 mg (yield 24%) of 1a-acetyl-7-demethoxy-6-demethyl-7-ethylenedioxy-6,7-dihydro-6-n-propylmitomycin A as a yellowish pink powder.

The whole amount of the product obtained above was dissolved in 10 ml of methanol and 1.0 ml of a 6.1M solution of ammonia in methanol. The resulting solution was allowed to stand at 20° C. for 22 hours and 20 minutes and at 5° C. for 40 hours. The reaction mixture was concentrated in vacuo. The residue obtained was purified by preparative TLC (silica gel; chloroform:methanol=9:1) to give a violet fraction containing the desired product. This fraction was extracted, cystallized with dichloromethane and fully dried in vacuo in a conventional manner to give 12.7 mg (yield, 14%) of Compound 4 as violet needles. The filtrate was treated by conventional procedure to give a powder and dried in vacuo to give 13.9 mg (yield, 16%) of the product as a violet powder.

TLC: $R_f=0.43$ (chloroform:methanol=9:1) EI-MS m/z 362 (M+); $C_{17}H_{22}N_4O_5=362$ IR (cm$^{-1}$): 3430, 3320, 3280, 3200, 2950, 2860, 1710, 1600, 1560, 1550, 1450, 1370, 1340, 1070 $^1$H-NMR (270 MHz, pyridine-d$_5$) δ(ppm): 0.84 (t, J=7.3 Hz, 3H), 1.45–1.65 (m, 2H), 1.9–2.2 (br, 1H), 2.56 (bt, J=7.7 Hz, 2H), 2.73 (bs, 1H), 3.13 (bs, 1H), 3.21 (s, 3H), 3.60 (bd, J=13.4 Hz, 1H), 4.03 (dd, J=4.1 & 11.1 Hz, 1H), 4.57 (d, J=12.7 Hz, 1H), 5.0–5.2 (br, 1H), 5.42 (dd, J=4.3 & 10.4 Hz, 1H), 7.3–7.8 (br, 4H)

Example 5

Synthesis of 6-allyl-6-demethyl-mitomycin C
(Compound 5)

After Compound b (56.0 mg) obtained in REFERENCE EXAMPLE 2 was dissolved in 1.0 ml of anhydrous acetone, 100 μl of allyl iodide and 65 mg of cesium carbonate were added to the solution. The mixture was stirred at 20° C. for 40 hours and a half. The reaction mixture was diluted with chloroform, washed successively with a phosphate buffer (pH 4), saturated aqueous sodium hydrogencarbonate solution and saturated aqueous sodium chloride solution, and then dried over anhydrous sodium sulfate. After the solvent was distilled off, the residue was purified by preparative TLC (silica gel; chloroform:methanol =9:1) to give a yellow fraction. This fraction was treated in a conventional manner to give 30.1 mg (yield 50%) of 1a-acetyl-6-allyl-7-demethoxy-6-demethyl-7-ethylenedioxy-6, 7-dihydro-6-phenylselenomitomycin A as a yellow powder. The purity of the compound was about 70% by $^1$H-NMR.

23.9 mg of the product obtained above was dissolved in 2.0 ml of a 6.1M solution of ammonia in methanol and 40 mg of dimedone was added to the solution. The mixture was stirred at 20° C. for 20 hours. After diluting the reaction mixture with dichloromethane, the organic layer was washed with saturated aqueous sodium chloride solution. The reaction mixture was then dried over anhydrous sodium sulfate. After the solvent was distilled off, the residue was purified by preparative TLC (silica gel; chloroform:methanol=9:1) to give a violet fraction containing the desired product. This fraction was treated in a conventional manner to give 4.6 mg (yield, about 46%) of Compound 5 as a violet powder.

TLC: Rf=0.25 (chloroform:methanol=9:1) FAB-MS (m/z): 361 (M++1); $C_{17}H_{20}N_4O_5=360$ IR (cm$^{-1}$): 3420, 3320, 3200, 2920, 2850, 1720, 1710, 1600, 1560, 1550, 1450, 1440, 1370, 1340, 1230, 1070 $^1$H-NMR (270 MHz, pyridine-d$_5$) δ(ppm): 2.07 (bs, 1H), 2.73 (bs, 1H), 3.16 (bs, 1H), 3.21 (s, 3H), 3.3–3.5 (m, 2H), 3.59 (bd, J=12.3 Hz, 1H), 4.04 (dd, J=4.1 & 11 .1 Hz, 1H), 4.56 (d, J=12.6 Hz, 1H), 4.99 (dd, J=1.5 & 9.9 Hz, 1H), 5.12 (bt, J=11 Hz, 1H), 5.21 (dd, J=1.7 & 19.0 Hz, 1H), 5.43 (dd, J=4.2 & 10.4 Hz, 1H), 5.85–6.02 (m, 1H), 7.3–7.8 (br, 4H)

Example 6

Synthesis of 6-demethyl-6-n-pentylmitomycin C (Compound 6)

After 190 mg of Compound a obtained in REFERENCE EXAMPLE 1 was dissolved in 6.0 ml of anhydrous tetrahydrofuran, 5.3 ml of a 0.094M solution of lithium di-n-butyl cuprate in tetrahydrofuran was added dropwise at $-78°$ C. over 30 minutes. The mixture was stirred at $-78°$ C. for 50 minutes. Saturated aqueous ammonium chloride solution was added to the reaction mixture. The mixture was stirred and then extracted with chloroform. The organic layer was washed with saturated aqueous sodium chloride solution and dried over anhydrous sodium sulfate and then the solvent was distilled off. The residue obtained was purified by column chromatography (silica gel; chloroform:methanol=50:1 to 30:1)to give a red fraction. This fraction was treated in a conventional manner to give 74.4 mg (yield, 34%) of a 1a-acetyl-7-demethoxy-6-demethyl-7-ethylenedioxy-6, 7-dihydro-6-n-pentylmitomycin A as a pink powder.

The whole amount of the product obtained above was dissolved in 4.8 ml of a 6.8M solution of ammonia in methanol. The resulting solution was allowed to stand at 20° C. for 23 hours. After the solvent was distilled off, the residue obtained was purified by column chromatography (silica gel; chloroform:methanol=30:1) to give a violet fraction. This fraction was treated in a conventional manner to give 28.2 mg (yield 46%) of Compound 6 as a violet powder.

TLC: $R_f=0.37$ (chloroform:methanol=9:1) SI-MS (m/z): 392 (M$^+$+2); $C_{19}H_{26}N_4O_5=390$ IR (cm$^{-1}$): 3400, 3320, 2930, 1700, 1650, 1590, 1540, 1450, 1340, 1270, 1220, 1070 $^1$H-NMR (400 MHz, chloroform - d$_1$) δ(ppm): 0.65 (br, 1H), 0.89 (t, J=6.9 Hz, 3H), 1.26–1.40 (m, 6H), 2.20–2.24 (m, 2H), 2.82 (br, 1H), 2.89 (d, J=4.4 Hz, 1H), 3.22 (s, 3H), 3.51 (bd, J=12.8 Hz, 1H), 3.62 (dd, J=4.4 & 10.6 Hz, 1H), 4.25 (d, J=12.8 Hz, 1H), 4.54 (bt, J=10.6 Hz, 1H), 4.69 (br, 2H), 4.71 (dd, J=4.4 & 10.6 Hz, 1H), 5.24 (br, 2H)

Example 7

Synthesis of 6-benzyl-6-demethylmitomycin C (Compound 7)

After Compound b (28.1 mg) obtained in REFERENCE EXAMPLE 2 was dissolved in 0.50 ml of anhydrous acetone, 60 μl of benzyl bromide and 35 mg of cesium carbonate were added to the solution. The mixture was stirred at 20° C. for 13 hours. After the reaction mixture was diluted with chloroform, the dilution was washed successively with saturated aqueous sodium hydrogencarbonate solution and saturated aqueous sodium chloride solution. The reaction mixture was then dried over anhydrous sodium sulfate. After the solvent was distilled off, the residue was purified by preparative TLC (silica gel; chloroform:acetonitrile:n-hexane=5:5:1) to give a yellow fraction. This fraction was treated in a conventional manner to give 15.3 mg of the crude product containing 1a-acetyl-6-benzyl-7-demethoxy-6-demethyl-6,7-dihydro-6-phenyl-selenomitomyc A as a yellow powder.

The whole amount of the crude product obtained was dissolved in 1.0 ml of a 6.1M solution of ammonia in methanol and 10 mg of dimedone was added. The reaction mixture was stirred at 20° C. for 40 minutes and then diluted with dichloromethane. Subsequently, the dilution was washed with saturated aqueous sodium chloride solution and dried over anhydrous sodium sulfate. After the solvent was distilled off, the residue obtained was purified by preparative TLC (silica gel; chloroform:methanol=9:1) to give a violet fraction containing the desired product. This fraction was treated in a conventional manner to give 4.5 mg (yield 22%) of Compound 7 as a violet powder.

TLC: $R_f=0.44$ (chloroform:methanol=9:1) FAB-MS (m/z): 411 (M$^+$+1); $C_{21}H_{22}N_4O_5=410$ IR (cm$^{-1}$): 3420, 3320, 2920, 1720, 1710, 1600, 1560, 1550, 1450, 1440, 1370, 1340, 1220, 1070 $^1$H-NMR (270 MHz, pyridine-d$_5$) δ(ppm): 2.05 (bs, 1H), 2.72 (bs, 1H), 3.13 (bs, 1H), 3.19 (s, 3H), 3.58 (bd, J=12.3 Hz, 1H), 3.96 (d, J=15.4 Hz, 1H), 4.04 (d, J=15.4 Hz, 1H), 4.04 (dd, J=4.4 & 11.4 Hz, 1H), 4.55 (d, J=12.6 Hz, 1H), 5.12 (bt, J=11 Hz, 1H), 5.42 (dd, J=4.3 & 10.3 Hz, 1H), 7.08–7.26 (m, 3H), 7.41–7.57 (m, 2H), 7.4–7.8 (br, 2H), 7.7 (bs, 2H)

Example 8

Synthesis of 6-demethyl-6-(2-nitroethyl)mitomycin C (Compound 8)

Compound a (1.00 g) obtained in REFERENCE EXAMPLE 1 was dissolved in 50 ml of dichloromethane, and 660 mg of potassium carbonate and 2.5 ml of nitromethane were added to the solution. The mixture was stirred at 20° C. for 2 hours and a half. The reaction mixture was washed with saturated aqueous sodium chloride solution and then dried over anhydrous sodium sulfate. The solvent was then distilled off. The residue obtained was purified by column chromatography (silica gel; chloroform:methanol=20:1) to give a yellow fraction. This fraction was treated in a conventional manner to give 547.7 mg (yield 48%) of 1a-acetyl-7-demethoxy-6-demethyl-7-ethylenedioxy-6, 7-dihydro-6-(2-nitroethyl)mitomycin A as a yellow powder.

The whole amount of the product above was dissolved in 50 ml of anhydrous tetrahydrofuran and the solution was allowed to stand at 20° C. for 70 hours under anhydrous ammonia atmosphere. The solvent was distilled off from the reaction mixture. The residue obtained was purified by column chromatography (silica gel; chloroform: methanol=20:1 to 10:1) to give a violet fraction. From this fraction the solvent was distilled off and the residue was crystallized from methanol-dichloromethane to give 123.6 mg (yield 28%) of Compound 8 as violet prisms.

TLC: $R_f 0.22$ (chloroform:methanol=9:1) SI-MS (m/z): 395 (M$^+$+2); $C_{16}H_{19}N_5O_7=393$ IR (cm$^{-1}$): 3420, 3340, 2940, 1710, 1660, 1600, 1560, 1540, 1480, 1450, 1370, 1330, 1190, 1170, 1060 $^1$H-NMR(400 MHz, pyridine-d$_5$) δ(ppm): 2.23 (br, 1H), 2.77 (br, 1H), 3.15 (br, 1H), 3.22 (s, 3H), 3.27–3.40 (m, 2H), 3.60 (bd, J=12.3 Hz, 1H), 4.03 (dd, J=4.2 & 11.1 Hz, 1H), 4.54 (d, J=12.8 Hz, 1H), 4.70 (t, J=7.6 Hz, 2H), 5.09 (bt, J=10.3 Hz, 1H), 5.42(dd, J=4.2 & 10.3 Hz, 1H), 7.63 (br, 2H), 8.20 (br, 2H)

Example 9

Synthesis of Compound 9

422 mg of Compound a obtained in REFERENCE EXAMPLE 1 was dissolved in 30 ml of anhydrous tetrahydrofuran and 152 mg of dimedone and 100 μl of anhydrous triethylamine were added to the solution followed by stirring at ambient temperature for 45 minutes. The reaction mixture was washed with saturated aqueous sodium chloride solution and then dried over anhydrous sodium sulfate. The solvent was then distilled off. The residue was purified by column chromatography (silica gel; chloroform: methanol=20:1 to 10:1)to give violet to yellow fractions. The fractions were treated in a conventional manner to give the crude product (378.7 mg) containing 1a-acetyl-7-demethoxy-6-demethyl-6-[(4,4-dimethylcyclohexane-2,6-dion-1-yl)-7-ethylenedioxy-6, 7-dihydro methyl]mitomyc A as a violet powder.

The product (241.2 mg) obtained above was dissolved in 10 ml of a 6.1M solution of ammonia in methanol and 100 mg of dimedone was added to the solution. The mixture was stirred at 20° C. for 3 hours. The reaction mixture was concentrated in vacuo and chloroform was added to the concentrate to form a solution. The solution was washed with saturated aqueous sodium chloride solution. The aqueous layer was allowed to stand for a while and extracted with chloroform after the solution was turned violet. The organic layers were combined and dried over anhydrous sodium sulfate. The solvent was distilled off. The residue obtained was purified by preparative TLC (silica gel; chloroform methanol=9:1) to give a green fraction. This fraction was treated in a conventional manner to give 51.6 mg (yield, 17%) of the product as a green powder.

TLC: $R_f$=0.47 (chloroform:methanol=9:1) FAB-MS (m/z):474 (M$^+$+2); $C_{23}H_{28}N_4O_7$=472 IR (cm$^{-1}$): 3400, 3170, 2950, 2880, 1720, 1710, 1610, 1560, 1520, 1450, 1350, 1240, 1220, 1160, 1060 $^1$H-NMR (270 MHz, pyridine-$d_5$) δ(ppm): 0.92 (s, 6H), 2.11 (bs, 1H), 2.33 (s, 4H), 2.75 (bs, 1H), 3.12 (bs, 1H), 3.18 (s, 3H), 3.37 (d, J=15.0 Hz, 1H), 3.45 (d, J=15.0 Hz, 1H), 3.58 (bd, J=12.7 Hz, 1H), 3.96 (dd, J=4.3 & 11.1 Hz, 1H), 4.45 (d, J=12.9 Hz, 1H), 5.02 (bt, J=11 Hz, 1H), 5.33 (dd, J=4.3 & 10.4 Hz, 1H), 7.4–7.8 (br, 2H), 8.62 (bs, 1H), 8.95(bs, 1H), 14.5 (br, 1H)

Example 10

Synthesis of Compound 10

After 216 mg of Compound a obtained in REFERENCE EXAMPLE 1 was dissolved in 10 ml of anhydrous tetrahydrofuran, a solution of ethyl 2-methylacetoacetate sodium salt separately prepared from 191 mg of sodium hydride (60% content, oil dispersion) and 0.68 ml of ethyl 2-methylacetoacetate in tetrahydrofuran was added to the solution at 0° C. The mixture was stirred at 20° C. for 20 minutes. The reaction mixture was poured into a phosphate buffer (pH 4) followed by extraction with chloroform. The chloroform layer was washed with saturated aqueous sodium hydrogencarbonate solution, and dried over anhydrous sodium sulfate, and then the solvent was distilled off. The residue obtained was purified by column chromatography (silica gel; chloroform:methanol=50:1)to give 160 mg (yield, 56%) of 1a-acetyl-6-[2-acetyl-2-(ethoxy-carbonylpropyl)]-7-demethoxy-6-demethyl-7-ethylenedioxy-6, 7-dihydromitomycin A.

The whole amount of the product obtained was dissolved in 20 ml of methanol and 8 mg of potassium carbonate was added to the solution. The mixture was stirred at 0° C. for 3 hours. The reaction mixture was neutralized with a phosphate buffer (pH 6) followed by extraction with chloroform. The chloroform layer was dried over anhydrous sodium sulfate and the solvent was distilled off in vacuo. The residue obtained was purified by preparative TLC (silica gel; chloroform:methanol=30:1 to 20:1) to give 72 mg (yield, 50%) of the 1a-acetyl derivative of Compound 10.

The whole amount of the product was dissolved in 8 ml of tetrahydrofuran and 1 ml of saturated aqueous sodium hydrogencarbonate solution. The mixture was stirred at ambient temperature for 4 hours. Saturated aqueous sodium chloride solution was added to the reaction mixture followed by extraction with chloroform. The chloroform layer was dried over anhydrous sodium sulfate and the solvent was distilled off in vacuo. The residue obtained was purified by preparative TLC (silica gel; chloroform-methanol=20:1) to give 20 mg (yield, 31%) of Compound 10 as the mixture of diastereoisomers.

TLC: $R_f$=0.54 (chloroform:methanol=9:1) SI-MS (m/z): 493 (M$^+$+2); $C_{23}H_{29}N_3O_9$=491 IR (cm$^{-1}$): 3430, 2930, 1710, 1620, 1570, 1440, 1330, 1280, 1210, 1110, 1070 $^1$H-NMR (400 MHz, chloroform-$d_1$) δ(ppm): Diastereoisomer A:1.1–1.4 (br, 1H), 1.19 (s, 3H), 1.29 (t, J=7.1 Hz, 3H), 2.22 (s, 3H), 2.81 (dd, J=1.7 & 4.4 Hz, 1H), 2.90 (d, J=4.4 Hz, 1H), 2.98 (s, 2H), 3.22 (s, 3H), 3.45 (bd, J=12.8 Hz, 1H), 3.60 (dd, J=4.4 & 10.6 Hz, 1H), 4.00 (d, J=12.6 Hz, 1H), 4.06 (s, 3H), 4.15–4.27 (m, 2H), 4.54 (t, J=10.6 Hz, 1H), 4.73 (dd, J=4.4 & 10.6 Hz, 1H), 4.90 (br, 2H) Diastereoisomer B: 1.1–1.4 (br, 1H), 1.19 (s, 3H), 1.29(t, J=7.1 Hz, 3H), 2.21 (s, 3H), 2.81 (dd, J=1.7 & 4.4 Hz, 1 H), 2.90 (d, J=4.4 Hz, 1H), 2.98 (s, 2H), 3.22 (s, 3H), 3.45 (bd, J=12.8 Hz, 1H), 360 (dd, J=44 & 10.6 Hz, 1H), 3.97 (d, J=12.6 Hz, 1H), 4.06 (s, 3H), 4.15–4.27(m, 2H), 4.54 (t, J=10.6 Hz, 1H), 4.71 (dd, J=4.4 & 10.8 Hz, 1H), 4.90 (br, 2H)

Example 11

Synthesis of Compound 11

After 196 mg of Compound a obtained in REFERENCE EXAMPLE 1 was dissolved in 10 ml of chloroform, a solution of diethyl methylmalonate sodium salt separately prepared from 116 mg of sodium hydride (60% content, oil dispersion) and 0.49 ml of diethyl methylmalonate in tetrahydrofuran was added to the solution at 0° C. The mixture was stirred at 20° C. for an hour. The reaction mixture was poured into a phosphate buffer (pH 4) followed by extraction with chloroform. The chloroform layer was washed with saturated aqueous sodium hydogencarbonate solution, and dried over anhydrous sodium sulfate, and then the solvent was distilled off. The residue obtained was purified by column chromatography (silica gel; chloroform :methanol=30:1) to give 160 mg (yield, 58%) of 1a-acetyl-6-[2,2-bis (ethoxycarbonyl)propyl]-7-demethoxy-6-demethyl-6, 7-dihydro-7-ethylenedioxymitomycin A.

The whole amount of the product obtained was dissolved in 15 ml of ethanol and 1.0 ml of a 6.8M solution of ammonia in methanol was added to the solution. The mixture was stirred at 20° C for 10 hours. The solvent was distilled off in vacuo. The residue was purified by preparative TLC (silica gel; chloroform: methanol=94:6)to give 44 mg (yield, 35%) of Compound 11.

TLC: $R_f$=0.51 (chloroform:methanol:acetone=4.5:0.5:5.0) SI-MS(m/z): 463 (M$^+$+3); $C_{21}H_{24}N_4O_8$=460 IR (cm$^{-1}$): 3450, 2930, 1710, 1650, 1620, 1570, 1460, 1410, 1340, 1260, 1160, 1100, 1070 $^1$H-NMR (400 MHz, chloroform-$d_1$) δ(ppm): 0.90 (br, 1H), 1.23 (t, J=7.1 Hz, 3H), 1.49 (s, 3H), 2.55 (d, J=17.5 Hz, 1H), 2.88 (bd, J=4.7 Hz, 1H), 2.94 (d, J=4.7 Hz, 1H), 3.23 (s, 3H), 3.33 (d, J=17.5 Hz, 1H), 3.52 (dd, J=1.7 & 12.8 Hz, 1H), 3.66 (dd, J=4.7 & 10.3 Hz, 1H), 4.13(d, J=12.8 Hz, 1H), 4.20 (q, J=7.1 Hz, 2H), 4.56 (t, J=10.6 Hz, 1H), 4.67 (dd, J=4.7 & 10.6 Hz, 1H), 4.81 (br, 2H), 8.11 (br, 1H)

Example 12

Synthesis of Compound 12

After 196 mg of Compound a obtained in REFERENCE EXAMPLE 1 was dissolved in 5 ml of chloroform, a solution of ethyl acetoacetate sodium salt separately prepared from 70 mg of sodium hydride (60% content, oil dispersion) and 0.22 ml of ethyl acetoacetate in tetrahydrofuran was added to the solution at 0° C. The mixture was stirred at 20° C. for 1.5 hours. The reaction mixture was poured into a phosphate buffer (pH 4)followed by extraction with chloroform. The chloroform layer was washed with saturated aqueous sodium hydrogencarbonate solution, and dried over anhydrous sodium sulfate, and then the solvent was distilled off. The residue obtained was purified by column chromatography (silica gel; chloroform :methanol=50:1)to give 120 mg (yield, 47%) of the Ia-acetyl derivative of Compound 12.

150 mg of the product obtained was dissolved in 20 ml of methanol and 300 mg of ammonium acetate was added to the solution. The reaction mixture was poured into saturated aqueous sodium chloride solution followed by extraction with chloroform. The chloroform layer was dried over anhydrous sodium sulfate and the solvent was distilled off in vacuo. The residue was purified by preparative TLC (silica gel; chloroform :methanol=30:1)to give 23.8 mg (yield, 20%) of Compound 12.

TLC: $R_f$=0.40 (chloroform:methanol=9:1) SI-MS (m/z): 447 (M$^+$+2); $C_{21}H_{23}N_3O_8$=445 IR (cm$^{-1}$): 3450, 2910, 1720, 1650, 1630, 1570 1440, 1390, 1360, 1340, 1310, 1190, 1160, 1090, 1040 $^1$H-NMR (400 MHz, chloroform-d$_1$) δ(ppm): 0.60 (br, 1H), 1.31 (t, J=7.1 Hz, 3H), 2.38 (s, 3H), 2.85 (br, 1H), 2.91 (br, 1H), 3.09 (d, J=20.4 Hz, 1H), 3.20 (d, J=20.4 Hz, 1H), 3.23 (s, 3H), 3.45 (bd, J=12.3 Hz, 1H), 3.67 (dd, J=4.7 & 10.1 Hz, 1H), 4.07 (d, J=12.8 , 1H), 4.23 (q, J=7.1 Hz, 2H), 4.60 (bt, J=10.3 Hz, 1H), 4.70 (dd, J=4.7 & 10.6 Hz, 1H), 4.72 (br, 2H)

Example 13

Synthesis of Compound 13

1.03 g of Compound e obtained in REFERENCE EXAMPLE 5 was dissolved in 50 ml of anhydrous tetrahydrofuran and 0.20 ml of anhydrous triethylamine and 346 mg of dimedone were added to the solution followed by stirring at 20° C. for 40 minutes. The reaction mixture was diluted with saturated aqueous sodium chloride solution followed by extraction with chloroform. The organic layer was dried over anhydrous sodium sulfate and the solvent was distilled off. The residue was again dissolved in 100 ml of chloroform and 100 ml of silica gel was added to the solution to adsorb the product thereto. The reaction mixture was allowed to stand at ambient temperature for 15 hours. Silica gel was extracted with an eluent (chloroform: methanol=9:1) and the resultant violet solution was concentrated in vacuo. The residue was purified by column chromatography (silica gel; chloroform: methanol=50:1) to obtain a violet fraction. This fraction was treated in a conventional manner to give 634.9 mg (yield, 53%) of the la-allyloxycarbonyl derivative of Compound 13 as a violet powder.

To a solution of 251.9 mg of the compound above in 20 ml of tetrahydrofuran were added 0.200 ml of triethylammonium formate and 30 mg of tetrakis (triphenylphosphine) palladium (0) under argon atmosphere. The mixture was stirred at 20° C. for 22 minutes. The reaction mixture was applied directly to column chromatography (silica gel; chloroform :methanol=20:1)to give a reddish violet fraction. This fraction was treated in a conventional manner to give 110.2 mg (yield, 52%) of Compound 13 as a reddish violet powder.

TLC: $R_f$=0.29 (chloroform:methanol=9:1) FAB-MS (m/z): 456 (M$_+$+1); $C_{23}H_{25}N_3$7=455 IR (cm$^1$): 3450, 3300, 2950, 2880, 1720, 1710, 1660, 1630, 1570, 1380, 1330, 1200, 1070 $^1$H-NMR (270 MHz, pyridine-d$_5$) δ(ppm): 0.95 (s, 3H), 0.99 (s, 3H), 2.12 (bs, 1H), 2.33 (bs, 4H), 2.78 (bs, 1H), 3.08 (d, J=20.5 Hz, 1H), 3.16 (bs, 1H), 3.20 (d, J=20.7 Hz, 1H), 3.27(s, 3H), 3.53(bd, J=12 Hz, 1H), 4.06 (dd, J=4.4 & 11 .0 Hz, 1H), 4.18 (d, J=12.5 Hz, 1H), 5.12 (bt, J=10 Hz, 1H), 5.42 (dd, J=4.3 & 10.4 Hz, 1H), 7.4–7.8 (bs, 2H)

Example 14

Synthesis of Compound 14

840 mg of Compound a obtained in REFERENCE EXAMPLE 1 was dissolved in 50 ml of anhydrous tetrahydrofuran and 0.20 ml of anhydrous triethylamine and 231.6 mg of 1,3-cyclohexanedione were added to the solution followed by stirring at 20° C. for 3 hours. The reaction mixture was diluted with saturated aqueous sodium chloride solution followed by extraction with chloroform. After the organic layer was dried over anhydrous sodium sulfate, the solvent was distilled off. The residue was purified by column chromatography (silica gel; chloroform :methanol=20:1) to give a violet fraction. This fraction was treated in a conventional manner to give 591.7 mg (yield, 63%) of the la-acetyl derivative of Compound 14 as a violet powder.

The product (552.1 mg) obtained above was dissolved in 50 ml of methanol and 323.5 mg of potassium carbonate was added to the solution followed by stirring at −20° C. for 1.25 hours. The reaction mixture was diluted with a phosphate buffer (pH 4), which was then extracted with chloroform. The organic layer was dried over anhydrous sodium sulfate and the solvent was distilled off. The residue was purified by column chromatography (silica gel; chloroform:methanol=30:1) to give a reddish violet fraction. This fraction was again purified by preparative TLC (silica gel; chloroform :methanol=9:1) and then treated in a conventional manner to give 70.4 mg (yield, 14%) of Compound 14 as a red violet powder.

TLC: $R_f$=0.36 (chloroform:methanol=9:1) FAB-MS (m/z): 429 (M$^+$+2); $C_{21}H_{21}N_3O_7$=427 IR (cm$^{-1}$): 3450, 3350, 3330, 3200, 2950, 2880, 1720, 1660, 1630, 1570, 1450, 1380, 1340, 1210, 1190, 1120, 1070 $^1$H-NMR (270 MHz, pyridine-d$_5$) δ (ppm): 1.7–1.9 (m, 2H), 2.13 (bs, 1H), 2.3–2.5 (m, 4H), 2.79 (bs, 1H), 3.10–3.25 (m, 3H), 3.27 (s, 3H), 3.53 (bd, J=12 Hz, 1H), 4.04 (dd, J=4.3 & 11.1 Hz, 1H), 4.18 (d, J=12.5 Hz, 1H), 5.09 (bt, J=11 Hz, 1H), 5.39 (dd, J=4 & 3 & 10.4 Hz, 1H 7.1–7.8 (br, 2H)

Example 15

Synthesis of 6-demethyl-6-ethylmitomycin A (Compound 15)

After 843 mg of Compound a obtained in REFERENCE EXAMPLE 1 was dissolved in 100 ml of anhydrous tetrahydrofuran, 1.94 g of phenol was added to the solution. With stirring at $-78°$ C., 40 ml of a 0.25M solution of lithium dimethyl cuprate in tetrahydrofuran was added dropwise to the solution over 50 minutes. The mixture was stirred for 30 minutes at the same temperature.

Saturated aqueous ammonium chloride solution was added to the yellowish orange reaction mixture. After the resulting reddish pink solution was separated, the aqueous layer was extracted with chloroform. The organic layer was washed with saturated aqueous sodium chloride solution and dried over anhydrous sodium sulfate. The desiccant was removed by filtration and the solvent was distilled off. The residue was purified by column chromatography (silica gel: chloroform:methanol=30:1 to 20:1)to give a yellowish pink fraction containing the desired product. n-Hexane-chloroform was added to this fraction to give a powder. The solvent was distilled off and the residue was thoroughly dried in vacuo to give 382.6 mg (yield, 44%) of la-acetyl-7-demethoxy-6-demethyl-6-ethyl-7-ethylenedioxy-6,7-dihydro mitomycin A as a yellowish pink powder.

371.9 mg of the product obtained above was dissolved in 40 ml of methanol and 237 mg of potassium carbonate was added to the solution. The mixture was stirred at ambient temperature for 2 hours and 50 minutes.

Saturated aqueous sodium chloride solution was added to the reaction mixture and the mixture was extracted with chloroform. The organic layer was washed with saturated aqueous sodium chloride solution and dried over anhydrous sodium sulfate. The desiccant was removed by filtration and the solvent was distilled off. The residue was purified by column chromatography (silica gel; chloroform :acetone=2:1) to give a violet fraction containing the desired product. After the solvent was distilled off from this fraction, n-hexane-chloroform was added to give a powder. The solvent was distilled off and the residue was thoroughly dried in vacuo to give 187.1 mg (yield, 60%) of Compound 15 as a violet powder.

TLC: $R_f=0.32$ (chloroform:acetonitrile:n-hexane=5:5:1) FAB-MS (m/z): 365 (M$^+$+2); $C_{17}H_{21}N_3O_6=363$ IR (cm$^{-1}$): 3450, 3300, 2950, 1740, 1710, 1650, 1630, 1570, 1330, 1270, 1220, 1050 $^1$H-NMR (270 MHz, pyridine-d$_5$) δ(ppm): 0.98 (t, J=7.2 Hz, 3H), 2.15(bt, J=7.4 Hz, 1H), 2.40 (q, J=7.2 Hz, 2H), 2.78 (bs, 1H), 3.15 (dd, J=4.5 & 7.4 Hz, 1H), 3.23(s, 3H), 3.54 (bd, J=ca. 12 Hz, 1H), 4.01 (dd, J=4.2 & 10.9 Hz, 1H), 4.04 (s, 3H), 4.24 (d, J=12.4 Hz, 1H), 5.09 (bt, J=ca. 11Hz, 1H), 5.42 (dd, J=4.2 & 10.1 Hz, 1H), 7.3-8.0(br, 2H)

Example 16

Synthesis of 6-demethyl-6-ethylmitomycin B (Compound 16)

After 375 mg of 7-demethoxy-6-demethyl-6,7-dihydro-6-ethyl-7-ethylenedioxymitomycin B obtained in EXAMPLE 3 was dissolved in solution followed by stirring at ambient temperature for 4 hours and 10 minutes.

The reaction mixture was subjected to the same work-up as in EXAMPLE 15. The residue obtained was purified by column chromatography (silica gel; chloroform:methanol=20:1) to give a violet fraction containing the desired product. After the solvent was distilled off from this fraction, n-hexane-chloroform was added to the residue to give a powder. The solvent was distilled off and the residue was thoroughly dried in vacuo to give 143.6 mg (yield, 41%) of Compound 16 as a violet powder.

TLC: $R_f=0.33$ (chloroform:methanol=9:1) FAB-MS (m/z): 366 (M$^+$+3); $C_{17}H_{21}N_3O_6=363$ IR (cm$^{-1}$): 3440, 3300, 3200, 2950, 1740, 1700, 1650, 1620, 1570, 1460, 1450, 1340, 1260, 1110, 1060, 1040 $^1$H-NMR (270 MHz, pyridine-d$_5$) δ(ppm):0.92 (t, J=7.7 Hz, 3H), 2.11 (s, 3H), 2.24 (dd, J=2.0 & 4.5 Hz, 1H), 2.3-2.4 (m, 2H), 2.48 (d, J=4.5 Hz, 1H), 3.60 (dd, J=2.0 & 12.9 Hz, 1H), 4.00 (s, 3H), 4.16 (d, J=12.4 Hz, 1H), 4.24 (dd, J=3.5 & 9.9 Hz, 1H), 5.21 (t, J=10.1 Hz, 1H), 5.46 (dd, J=3.5 & 10.4 Hz, 1H), 7.3-7.7 (br, 2H), 8.28 (s, 1H)

Example 17

Synthesis of 6-demethyl-6-(2-methylpropyl)mitomycin C (Compound 17)

To a solution of 907 mg of Compound e obtained in REFERENCE EXAMPLE 5 in 30 ml of anhydrous tetrahydrofuran, was added 113 mg of copper (I) iodide. The mixture was cooled to $-78°$ C. While stirring, 5.0 ml of a 0.67M solution of isopropylmagnesium bromide in tetrahydrofuran was added dropwise to the solution over an hour. After reaction mixture was stirred at $-78°$ C. for 20 minutes. 1.5 ml of the solution of isopropyl magnesium bromide in tetrahydrofuran was additionally added dropwise to the reaction mixture over 25 minutes and the resulting mixture was stirred at $-78°$ C. for 5 minutes.

Saturated aqueous ammonium chloride solution was added to the yellowish orange reaction mixture. After the resultant reddish pink solution was separated, the aqueous layer was extracted with chloroform. The organic layer was washed with saturated aqueous sodium chloride solution, and dried over anhydrous sodium sulfate. The desiccant was removed by filtration, and the solvent was distilled off. The residue obtained was purified by column chromatography (silica gel; chloroform:methanol=20:1) to give a yellowish pink fraction containing the desired product. n-Hexane-chloroform was added to the mixture to give a powder. The solvent was distilled off and then thoroughly dried in vacuo to give 587.2 mg (yield, 59%) of la-alloxycarbonyl-7-demethoxy-6-demethyl-7-ethylenedioxy-6,7-dihydro-6-(2-methylpropyl)mitomycin A as a yellowish pink powder.

259.6 mg of the product obtained above was dissolved in 30 ml of anhydrous tetrahydrofuran. The solution was allowed to stand for 137.5 hours at ambient temperature under anhydrous ammonia atmosphere.

The reaction mixture was concentrated under reduced pressure and the residue obtained was purified by preparative TLC (silica gel: chloroform:methanol=9:1) to give a violet fraction containing the desired product. This fraction was extracted with the developing solvent and the solvent was distilled off. Then, n-hexane-chloroform was added to the residue to give a powder. After stripping the solvent, the residue was thoroughly dried in vacuo to give 163.2 mg (yield, 69%) of la-allyloxycarbonyl derivative of Compound 17 as a violet powder.

191.8 mg of the product obtained above was dissolved in 20 ml of anhydrous tetrahydrofuran, and 0.20 ml of triethylammonium formate and a solution of 30 mg of tetrakis (triphenylphosphine) palladium (0) in 2.0 ml of anhydrous tetrahydrofuran-was added to the solution. The mixture was stirred at ambient temperature for an hour and 10 minutes under an argon atmosphere.

The reaction mixture was purified directly by column chromatography (silica gel; chloroform :methanol=30:1 to 20:1 ). The solvent was distilled off from the resulting violet fraction. Then, n-hexane-chloroform was added to give a powder. After stripping solvent, the residue was thoroughly dried in vacuo to give 112.2 mg (yield, 72%) of compound 17 as a violet powder.

TLC: $R_f$=0.29 (chloroform:methanol=9:1) FAB-MS (m/z): 377 (M++1); $C_{18}H_{24}N_4O_5$=376 IR (cm$^{-1}$): 3480, 3440, 3430, 3330, 3280, 2950, 1730, 1600, 1560, 1450, 1370, 1330, 1070 $^1$H-NMR (270 MHz, pyridine-d$_5$) δ(ppm): 0.91 (d, J=6.4 Hz, 6H), 1.95-2.16 (m, 2H), 2.51 (d, J=7.4 Hz, 2H), 2.74 (bs, 1H), 3.15 (bs, 1H), 3.21 (s, 3H), 3.61 (bd, J=ca. 13 Hz, 1H), 4.05 (dd, J=4.5 & 10.9 Hz, 1H), 4.58 (d, J=12.9 Hz, 1H), 5.13 (bt, J=ca.10 Hz, 1H), 5.45 (dd, J=10.4 Hz, 1H), 7.3-7.9 (br, 4H)

Example 18

Synthesis of 6-demethyl-6-(2-methylpropyl)mitomycin A (Compound 18)

After 400.2 mg of la-allyloxycarbonyl-7-demethoxy-6-demethyl-7-ethylenedioxy-6, 7-dihydro-6-(2-methylpropyl)mitomycin A was dissolved in 25 ml of anhydrous tetrahydrofuran, 1.0 ml of triethylammonium formate and a solution of 94 mg of tetrakis (triphenylphosphine) palladium (0) in 4.5 ml of tetrahydrofuran were added to the solution in 3 portions, respectively. The mixture was stirred for 3 hours at ambient temperature under an argon atmosphere.

The reaction mixture was applied directly to column chromatography (silica gel; chloroform; methanol=50:1 to 20:1)to give a fraction containing the desired product. The solvent was distilled off from this fraction. Chloroform-n-hexane was added to the residue to give a powder. The solvent was distilled off and the residue was thoroughly dried in vacuo to give 247 mg of crude 7-demethoxy-6-demethyl-7-ethylenedioxy-6,7-dihydro-6-(2-methylpropyl)mitomycin A as a yellowish pink powder.

The crude product (223.8 mg, 90.6% of the whole amount) obtained above was dissolved in 30 ml of methanol and 148 mg of potassium carbonate was added to the solution followed by stirring at ambient temperature for an hour.

The reaction mixture was subjected to work-up as in EXAMPLE 15. The residue obtained was purified by column chromatography (silica gel; chloroform:acetonitrile:n-hexane=5:5:1) to give a reddish violet fraction containing the desired product. After the solvent was distilled off from this fraction, chloroform-n-hexane was added to give a powder. The solvent was distilled off and the residue was thoroughly dried in vacuo to give 36.7 mg (yield, 18%) of Compound 18 as a reddish as a reddish violet powder.

TLC: $R_f$=0.44 (chloroform:methanol=9:1) FAB-MS (m/z): 392 (M++1); $C_{19}H_{25}N_3O_6$=391 IR (cm$^{-1}$): 3450, 3350, 3300, 2950, 1720, 1710, 1650, 1630, 1570, 1460, 1450, 1410, 1340, 1310, 1240, 1080, 1070, 1040 $^1$H-NMR (270 MHz, pyridine-d$_5$) δ(ppm): 0.86 (d, J=6.4 Hz, 6H), 1.85(m, 1H), 2.12 (m, 1H), 2.35(m, 2H), 2.77(bs, 1H), 3.15(bs, 1H), 3.22 (s, 3H), 3.55 (bd, J=12.4 Hz, 1H), 4.01 (dd, J=4.5 & 11.4 Hz, 1H), 4.07 (s, 3H), 4.25 (bd, J=12.4 Hz, 1H), 5.08 (bt, J=10.6 Hz, 1H), 5.42 (dd, J=4.5 & 10.4 Hz, 1H), 7.4-7.9(br, 2H)

Example 19

Synthesis of 6-demethyl-6-(2-methylpropyl) mitomycin B (Compound 19)

After 645 mg of Compound c obtained in REFERENCE EXAMPLE 3 was dissolved in 50 ml of anhydrous tetrahydrofuran, with stirring at −78° C., 3.0 ml of a 0.67M solution of isopropyl magnesium bromide in tetrahydrofuran was added dropwise to the solution over 15 minutes. The mixture was stirred for an hour and 40 minutes under the same conditions.

The reaction mixture was subjected to work-up as in EXAMPLE 17. The residue obtained was purified by column chromatography (silica gel; chloroform: methanol=30:1 to 20:1) to give a yellowish pink fraction containing the desired product. Chloroform-n-hexane was added to the fraction to give a powder. The solvent was distilled off and the residue was thoroughly dried in vacuo to give 171 mg (yield, 30% based on 7-demethoxy-7-ethylenedioxy-6, 7-dihydro-6-phenyl-selenomitomycin B) of 7-demethoxy-6-demethyl-7-ethylenedioxy-6,7-dihydro-6-(2-methylpropyl)mitomycin B as a yellowish pink powder.

After 161.4 mg of the product obtained above was dissolved in 30 ml of methanol, 110 mg of potassium carbonate was added to the solution followed by stirring at ambient temperature for 55 minutes.

The reaction mixture was subjected to work-up as in EXAMPLE 15. The residue obtained was purified by preparative TLC (silica gel; chloroform :methanol=9:1 ) to give a violet fraction containing the desired product. After the solvent was distilled off from this fraction, chloroform-n-hexane was added to give a powder. The solvent was distilled off and the residue was thoroughly dried in vacuo to give 63.3 mg (yield, 42%) of Compound 19 as a violet powder.

TLC:$R_f$=0.44 (chloroform:methanol=9:1) FAB-MS (m/z): 393 (M++2); $C_{19}H_{25}N_3O_6$=391 IR (cm$^1$): 3430, 3350, 3300, 2950, 1730, 1690, 1650, 1620, 1610, 1560, 1460, 1440, 1330, 1310, 1360, 1240, 1110 $^1$H-NMR (270 MHz, pyridine-d$^5$) δ(ppm): 0.82 (d, J=6.9 Hz, 6H), 1.78 (m, 1H), 2.10 (s, 3H), 2.24 (dd, J=2.0 & 5.0 Hz, 1H), 2.28 (m, 2H), 2.47 (d, J=5.0 Hz, 1H), 3.61 (dd, J=2.0 & 12.4 Hz, 1H), 4.02(s, 3H), 4.16(d, J=12.9 Hz, 1H), 4.25 (dd, J=3.5 & 9.4 Hz, 1H), 5.20 (bt, J=10.2 Hz, 1H), 5.44 (dd, J=3.5 & 10.9 Hz, 1H), 7.3-7.8 (br, 2H), 8.28 (s, 1H)

Example 20

Synthesis of 6-demethyl-6-n-pentylmitomycin A (Compound 20)

After 1.158 g of Compound e obtained in REFERENCE EXAMPLE 5 was dissolved in 80 ml of anhydrous tetrahydrofuran, 40 ml of a solution of lithium di-n-butyl cuprate in tetrahydrofuran-n-hexane (about 5.0 mmoles) was added dropwise to the solution over 30 minutes while stirring at −78° C. Subsequently, the mixture was stirred at −78° C. to −20° C. for 50 minutes.

The yellowish orange reaction mixture was subjected to work-up as in EXAMPLE 17. The residue obtained was purified by column chromatography (silica gel; chloroform:methanol=30:1) to give a yellowish pink fraction containing the desired product. Chloroform-n-hexane was added to this fraction to give a powder. The solvent was distilled off and the residue was thoroughly dried in vacuo to give 472.9 mg (yield, 43%) of 7-demethoxy-6-demethyl-7-ethylenedioxy-6, 7-dihydro-6-n-pentylmitomycin A as a yellowish pink powder.

After 403.2 mg of the product obtained above was dissolved in 50 ml of methanol, 511 mg of sodium hydrogen carbonate was added to the solution followed by stirring at ambient temperature for 23 hours and 20 minutes.

Chloroform was added to the reaction mixture and the precipitated inorganic salt was filtered off. After the solvent was distilled off, the residue was purified by column chromatography (silica gel; chloroform:methanol=50:1) to give a reddish violet fraction containing the desired product. After the solvent was distilled off from this fraction, chloroform-n-hexane was added to give a powder. The solvent was distilled off and the residue was thoroughly dried in vacuo to give 264.5 mg (yield, 70%) of Compound 20 as a reddish violet powder.

TLC: $R_f=0.37$ (chloroform:methanol=9:1) FAB-MS (m/z):406 ($M^+ +1$); $C_{20}H_{27}N_3O_6=405$ IR ($cm^{-1}$): 3400, 3300, 2950, 2900, 1740, 1700, 1650, 1630, 1580, 1570, 1450, 1430, 1410, 1340, 1320, 1270, 1220, 1070. $^1$H-NMR (270 MHz, chloroform-$d_1$) δ(ppm): 0.62 (bs, 1H), 0.89 (bt, J=6.9 Hz, 3H), 1.23-1.43 (m, 6H), 2.22-2.41 (m, 2H), 2.84 (bs, 1H), 2.91 (bs, 1H), 3.23 (s, 3H), 3.48 (bd, J=12.9 Hz, 1H), 3.62 (dd, J=4.6 & 10.6 Hz, 1H), 4.04 (s, 3H), 4.05 (d, J=12.9 Hz, 1H), 4.58 (bt, J=10.4 Hz, 1H), 4.74 (dd, J=4.6 & 10.4 Hz, 1H), 4.7-4.8 (br, 2H)

Example 21

Synthesis of 6-demethyl-6-n-pentylmitomycin B (Compound 21)

After 642 mg of Compound c obtained in REFERENCE EXAMPLE 3 was dissolved in 50 ml of anhydrous tetrahydrofuran, 2.0 g of phenol was added to the solution. While stirring at −78° C., 41 ml of a solution of lithium di-n-butyl cuprate in tetrahydrofuran-n-hexane (about 0.31M) was added dropwise to the solution over 15 minutes. Subsequently, the mixture was stirred for 25 minutes.

The reaction mixture was subjected to work-up as in EXAMPLE 17. The residue obtained was purified by column chromatography (silica gel; chloroform:methanol=30:1 to 10:1) to give a yellowish pink fraction containing the desired product. n-Hexane-chloroform was added to this fraction to give a powder. The solvent was distilled off and the residue was thoroughly dried in vacuo to give 174 mg (yield, 30% based on 7-demethoxy-7-ethylenedioxy-6, 7-dihydro-6-phenylselenomitomycin B) of 7-demethoxy-6-demethyl-7-ethylenedioxy-6, 7-dihydro-6-n-pentylmitomycin B as a yellowish pink powder.

After 164.9 mg of the product obtained above was dissolved in 30 ml of methanol, 108 mg of potassium carbonate was added to the solution followed by stirring at ambient temperature for 50 minutes.

The reaction mixture was subjected to work-up as in EXAMPLE 15. The residue obtained was purified by preparative TLC (silica gel; chloroform:acetone=1:1) to give a violet fraction containing the desired product. This fraction was extracted with the developing solvent and the solvent was distilled off. Then, chloroform-n-hexane was added to give a powder, the solvent was distilled off and the residue was thoroughly dried in vacuo to give 96.1 mg (yield, 63%) of Compound 21 as a violet powder.

TLC: $R_f=0.51$ (chloroform:methanol=9:1 ) FAB-MS (m/z):407 ($M^+ +2$) ;$C_{20}H_{27}N_3O_6=405$ IR ($cm^{-1}$): 3430, 3350, 3280, 2950, 2930, 2850, 1730, 1690, 1650, 1620, 1570, 1460, 1450, 1330, 1260, 1210, 1120 $^1$H-NMR (270 MHz, pyridine-$d_5$) δ(ppm): 0.80 (bt, J=6.9 Hz, 3H), 1.1-1.4 (m, 6H), 2.11 (s, 3H), 2.23 (dd, J=1.7 & 4.7 Hz, 1H), 2.3-2.4 (m, 2H), 2.47 (d, J=4.5 Hz, 1H), 3.60 (dd, J=2.0 & 12.9 Hz, 1H), 4.03 (s, 3H), 4.17 (d, J=12.9 Hz, 1H), 4.24 (dd, J=3.5 & 9.4 Hz, 1H), 5.20 (bt, J=10.2 Hz, 1H), 5.44 (dd, J=3.5 & 10.9 Hz, 1H), 7.3-7.7 (br, 2H), 8.24 (s, 1H)

Example 22

Synthesis of 6-benzyl-6-demethylmitomycin A (Compound 22)

After 845 mg of Compound a obtained in REFERENCE EXAMPLE 1 was dissolved in 100 ml of anhydrous tetrahydrofuran, 1.95 g of phenol was added to the solution. While stirring at −78° C., 30 ml of a solution of lithium diphenyl cuprate in tetrahydrofuran (about 0.34M) was added dropwise to the solution over 15 minutes. Subsequently, the mixture was stirred for 50 minutes.

The reaction mixture was subjected to work-up as in EXAMPLE 17. The residue obtained was purified by column chromatography (silica gel; chloroform:methanol=30:1) to give a yellowish pink fraction containing the desired product. n-Hexane-chloroform was added to give a powder. The solvent was distilled off and the residue was thoroughly dried in vacuo to give 584.1 mg (yield, 58%) of la-acetyl-6-benzyl-7-demethoxy-6-demethyl-7-ethylenedioxy-6, 7-dihydromitomycin A as a yellowish pink powder.

After 574.7 mg of the product obtained above was dissolved in 50 ml of methanol, 320 mg of potassium carbonate was added to the solution followed by stirring at ambient temperature for 1.5 hours.

The reaction mixture was subjected to work-up as in EXAMPLE 15. The residue obtained was purified by column chromatography (silica gel; chloroform:methanol=50:1 to 30:1) to give a reddish violet fraction containing the desired product. After the solvent was distilled off from this fraction, chloroform-n-hexane was added to give a powder, the solvent was distilled off and the residue was thoroughly dried in vacuo to give 238.4 mg (yield, 49%) of Compound 22 as a reddish violet powder.

TLC: $R_f=0.43$ (chloroform:methanol=9:1) SI-MS (m/z):426 ($M^+ +1$); $C_{22}H_{23}N_3O_6=425$ IR ($cm^{-1}$): 3450, 3370, 3300, 2950, 1720, 1710, 1630, 1570, 1450, 1440, 1340, 1330, 1320, 1220, 1070, 1050 $^1$H-NMR (270 MHz, pyridine-$d_5$)δ(ppm) :2.12 (bs, 1H). 2.74 (bs, 1H), 3.11 (bs, 1H) , 3.17 (s, 3H), 3.52 (bd, J=12.9 Hz, 1H), 3.75 (d, J=13.7 Hz, 1H).3.81 (d, J=13.7 Hz, 1H), 3.97 (dd, J=4.2 & 11.2 Hz, 1H), 4.07 (s, 3H). 4.21 (d, J=12.9 Hz. 1H), 5.04 (bt, J=ca. 11 Hz, 1H), 5.37 (dd. J=4.2 & 10.6 Hz, 1H), 7.15-7.35 (m, 3H), 7.40-7.45 (m. 2H), 7.3-7.9 (br, 2H)

Example 23

Synthesis of 6-demethyl-6-benzylmitomycin B (Compound 23)

After 963 mg of Compound c obtained in REFERENCE EXAMPLE 3 was dissolved in 100 ml of anhydrous tetrahydrofuran, 2.26 g of phenol was added to the solution. While stirring at −78° C., 40 ml of lithium diphenyl cuprate in tetrahydrofuran (about 0.34M) was added dropwise to the solution over 20 minutes. Subsequently, the mixture was stirred for 50 minutes.

The reaction mixture was subjected to work-up as in EXAMPLE 17. The residue obtained was purified by column chromatography (silica gel; chloroform:methanol=20:1) to give a yellowish pink fraction containing the desired product. n-Hexane-chloroform was added to give a powder. The solvent was distilled off and the residue was thoroughly dried in vacuo to give 208.2 mg (yield, 21% based on 7-demethoxy-7-ehylenedioxy-6, 7-dihydro-6-phenylselenomitomycin B) of 6-benzyl-7-demethoxy-6-demethyl-7-ethylenedioxy-6, 7-dihydromitomycin B as a yellowish pink powder.

After 194.5 mg of the product obtained above was dissolved in 30 ml of methanol, 128 mg of potassium carbonate was added to the solution followed by stirring at ambient temperature for an hour and 10 minutes.

The reaction mixture was subjected to work-up as in EXAMPLE 15. The residue obtained was purified by column chromatography (silica gel; chloroform:methanol=30:1) to give a violet fraction containing the desired product. After the solvent was distilled off from this fraction, chloroform-n-hexane was added to give a powder. The solvent was distilled off and the residue was thoroughly dried in vacuo to give 148.3 mg (yield, 82%) of Compound 23 as a violet powder.

TLC: $R_f$=0.33 (chloroform:methanol=9:1) FAB-MS (m/z):427 ($M^+$+2); $C_{22}H_{23}N_3O_6$=425 IR (cm$^{-1}$): 3400, 3330, 2900, 1750, 1740, 1660, 1600, 1490, 1450, 1370, 1310, 1240, 1110 $^1$H-NMR (270 MHz, pyridine-$d_5$) δ(ppm):2.09 (s, 3H), 2.22 (dd, J=1.6 & 4.5 Hz, 1H), 2.44 (d, J=4.5 Hz, 1H), 3.57 (dd, J=1.6 & 12.8 Hz, 1H), 3.71 (s, 2H), 4.01 (s, 3H), 4.10 (d, J=12.8 Hz, 1H), 4.21 (dd, J=3.5 & 9.9 Hz, 1H), 5.15 (t, J=10.1 Hz, 1H), 5.40 (dd, J=3.5 & 10.4 Hz, 1H), 7.10 -7.36 (m, 5H), 7.48 (bs, 2H), 8.26 (s, 1H)

Example 24

Synthesis of 6-demethyl-6-n-undecylmitomycin C (Compound 24)

After 808 mg of Compound a obtained in REFERENCE EXAMPLE 1 was dissolved in 20 ml of anhydrous tetrahydrofuran, 72 mg of copper (I) iodide was added to the solution. The mixture was cooled to −20° C. While stirring at this temperature, 6.0 ml of a 0.097M solution of n-decylmagnesium bromide in tetrahydrofuran was added dropwise to the solution over 50 minutes. Subsequently, the mixture was stirred for 30 minutes at −20° C. to 0° C.

The yellowish orange reaction mixture was subjected to work-up as in EXAMPLE 17. The residue obtained was purified by column chromatography (silica gel; chloroform:methanol=50:1)to give a yellowish pink fraction containing the desired product. n-Hexane-chloroform was added to this fraction to give a powder. The solvent was distilled off and the residue was thoroughly dried in vacuo to give 131.6 mg (yield, 12%) of la-acetyl-7-demethoxy-6-demethyl-7-ethylenedioxy-6, 7-dihydro-6-n-undecylmitomycin A as yellowish pink paste.

The whole amount of the product obtained above was dissolved in 20 ml of methanol and 5 ml of a 6.8M solution of ammonia in methanol and the solution was allowed to stand at ambient temperature for 17 hours and 40 minutes.

The reaction mixture was concentrated under reduced pressure. The residue obtained was purified by preparative TLC (silica gel: chloroform:methanol=9:1) to give a violet fraction containing the desired product. This fraction was extracted with the developing solvent. After the solvent was distilled off, n-hexane-chloroform was added to give a powder. The solvent was distilled off and the residue was thoroughly dried in vacuo to give 9.1 mg (yield, 8%) of Compound 24 as a violet powder.

TLC: $R_f$=0.31 (chloroform:methanol=9:1) FAB-MS (m/z): 476 ($M^+$+2), 515[($M^+$+2)+$K^+$]: $C_{25}H_{38}N_4O_5$=474 IR (cm$^{-1}$): 3450, 3330, 3200, 2920, 2850, 1720, 1710, 1600, 1570, 1550, 1450, 1360, 1340, 1070 $^1$H-NMR (270 MHz, pyridine-$d_5$) δ(ppm): 0.86 (t, J=6.6 Hz, 3H), 1.1–1.4 (m, 16H), 1.56 (m, 2H), 2.0–2.3 (br, 1H), 2.63 (m, 2H), 2.75 (bs, 1H), 3.15 (bs, 1H), 3.22 (s, 3H), 3.62 (bd, J=12.7 Hz, 1H), 4.06 (dd, J=4.2 & 11.2 Hz, 1H), 4.60 (d, J=12.7 Hz, 1H), 5.10 (bt, J=ca. 10 Hz, 1H), 5.46 (dd. J=4.2 & 10.3 Hz, 1H), 7.4–7.9 (br, 4H)

Example 25

Synthesis of 6-demethyl-6-n-undecylmitomycin A (Compound 25)

To a solution of 848 mg of Compound a obtained in REFERENCE EXAMPLE 1 in 100 ml of anhydrous tetrahydrofuran, was added 81 mg of copper (I) iodide. The mixture was cooled to −20° C. While stirring at −20° C., 7.0 ml of a 0.86M solution of n-decyl-magnesium bromide in tetrahydrofuran was added dropwise to the mixture over 30 minutes. Subsequently, the mixture was stirred for 20 minutes at 20° C.

The yellowish orange reaction mixture was subjected to work-up as in EXAMPLE 17. The residue obtained was purified by column chromatography (silica gel; chloroform:methanol=40:1 to 20:1) to give a yellowish pink fraction containing the desired product. The solvent was distilled off from this fraction and the residue was thoroughly dried in vacuo to give 495.1 mg of la-acetyl-7-demethoxy-6-demethyl-7-ethylenedioxy-6, 7-dihydro-6-n-undecylmitomycin A as yellowish pink paste.

The whole amount of the product obtained above was dissolved in 80 ml of methanol and 213 mg of potassium carbonate was added to the solution followed by stirring at ambient temperature for 4 hours.

The reaction mixture was subjected to work-up as in EXAMPLE 15. The residue obtained was purified by column chromatography (silica gel; chloroform:methanol=30:1) to give a reddish violet fraction containing the desired product. This fraction was extracted with the developing solvent. After the solvent was distilled off, n-hexane-chloroform was added to give a powder. The solvent was distilled off and the residue was thoroughly dried in vacuo to give 159.3 mg (yield, 16% based on Compound a) of Compound 25 as a reddish violet powder.

TLC: $R_f$=0.57 (chloroform:methanol=9:1) FAB-MS (m/z): 490 ($M^+$+1); $C_{26}H_{39}N_3O_6$=489 IR (cm$^{-1}$):

3450, 3350, 3300, 3200, 2920, 2850, 1720, 1650, 1630, 1580, 1450, 1340, 1070 $^1$H-NMR (270 MHz, pyridine-d$_5$) δ(ppm): 0.87 (bt, J=6.7 Hz, 3H), 1.0–1.4 (br, 16H), 1.43 (m, 2H), 2.0–2.2 (br, 1H), 2.45 (m, 2H), 2.76 (bs, 1H), 3.10 (bs, 1H), 3.22 (s, 3H), 3.54 (bd, J=ca,. 12 Hz, 1H), 3.96 (dd, J=4.4 & 11.1 Hz, 1H), 4.08 (s, 3H), 4.24 (d, J=12.4 Hz, 1H), 4.99 (bt, J=ca. 11 Hz, 1H), 5.34 (dd, J=4.4 & 10.4 Hz, 1H), 7.2–7.9 (br, 2H)

Example 26

Synthesis of 6-demethyl-6-n-nonadecylmitomycin C (Compound 26)

To a solution of 1,265 g of Compound a obtained in REFERENCE EXAMPLE 1 in 30 ml of anhydrous tetrahydrofuran, was added 96 mg of copper (I) iodide. The mixture was cooled to −78° C. While stirring −78° C. 8.0 ml of a 0.086M solution of octadecylmagnesium bromide in tetrahydrofuran was added dropwise to the mixture over 25 minutes. Subsequently, the mixture was stirred for 35 minutes at −78° C., and was stirred for further 40 minutes while elevating to ambient temperature.

The yellowish orange reaction mixture was subjected to work-up as in EXAMPLE 17. The residue obtained was purified by column chromatography (silica gel; chloroform:methanol=50:1) to give a yellowish pink fraction containing the desired product. n-Hexane-chloroform was added to give a powder. The solvent was distilled off and the residue was thoroughly dried in vacuo to give 404.6 mg (yield, 20%) of 1a-acetyl-7-demethoxy-6-demethyl-7-ethylenedioxy-6, 7-dihydro-6-n-nonadecylmitomycin A as a yellowish pink powder.

After 200.2 mg of the product obtained above was dissolved in the mixed solution of 20 ml of methanol and 5 ml of a 6.8M solution of ammonia in methanol. The resulting solution was allowed to stand at ambient temperature for 20 hours and 30 minutes.

The reaction mixture was concentrated under reduced pressure and the residue obtained was purified by column chromatography (silica gel: chloroform:methanol=40:1 to 30:1) and then by preparative TLC (silica gel; chloroform:methanol=9:1) to give a violet fraction containing the desired product. This fraction was extracted with the developing solvent and the solvent was distilled off. Then, n-hexane-chloroform was added to the mixture to give a powder. The solvent was distilled off and then the residue was thoroughly dried in vacuo to give 8.6 mg (yield, 5%) of Compound 26 as a violet powder.

TLC: R$_f$=0.38 (chloroform:methanol=9.1 ) FAB-MS(m/z): 587 (M$^+$+1); C$_{33}$H$_{54}$N$_4$O$_5$=586 IR (cm$^{-1}$): 3450, 3330, 3200, 2920, 2850, 1720, 1600, 1570, 1560, 1450, 1340, 1070 $^1$H-NMR (270 MHz, pyridine-d$_5$)δ(ppm): 0.87 (t, J=6.5 Hz, 3H), 1.1–1.5 (m, 32H), 1.56 (m, 2H), 2.0–2.2 (br, 1H), 2.63 (m, 2H), 2.74 (bs, 1H), 3.14 (bs, 1H), 3.22 (s, 3H), 3.61 (bd, J=ca. 13 Hz, 1H), 4.05 (dd, J=4.2 & 11.2 Hz, 1H), 4.60 (d, J=12.7 Hz, 1H), 5.11 (bt, J=ca. 10 Hz, 1H), 5.45(dd, J=4.3 & 10.4 Hz, 1H), 7.4–7.8 (br, 4H)

Example 27

Synthesis of 6-demethyl-6-n-nonadecylmitomycin A (Compound 27)

After 186.8 mg of 1a-acetyl-7-demethoxy-6-demethyl-7-ethylenedioxy-6, 7-dihydro-6-nonadecylmitomycin A was dissolved in 20 ml of methanol, 138 mg of potassium carbonate was added to the solution followed by stirring at ambient temperature for 6 hours and 40 minutes.

The reaction mixture was subjected to work-up as in EXAMPLE 15. The residue obtained was purified by column chromatography (silica gel; chloroform:methanol=50:1) and then by preparative TLC (silica gel: chloroform:methanol=9:1)to give a reddish violet fraction containing the desired product. This fraction was extracted with the developing solvent and the solvent was distilled off. Then, n-hexane-chloroform was added to give a powder. The solvent was distilled off and then the residue was thoroughly dried in vacuo to give 4.9 mg (yield, 3%) of Compound 28 as a reddish violet powder.

TLC: R$_f$=0.55 (chloroform:methanol=9:1) FAB-MS (m/z): 602 (M$^+$+1); C$_{34}$H$_{55}$N$_3$O$_6$=601 IR (cm$^{-1}$) :3450, 3420, 2920, 2850, 1710, 1630, 1570, 1470, 1450, 1340, 1220, 1070 $^1$H-NMR (270 MHz, pyridine-d$_5$)δ(ppm): 0.87 (t, J=6.7 Hz, 3H), 1.2–1.4 (m, 32H), 1.4–1.5(m, 2H), 2.13 (bs, 1H), 2.47(bt, J=6.6 Hz, 2H), 2.77 (bs, 1H), 3.15(bs, 1H), 3.24(s, 3H), 3.57(bd, J=12.5 Hz, 1H), 4.02 (dd, J=4.3 & 10.9 Hz, 1H), 4.10 (s, 3H), 4.28 (d, J=12.3 Hz, 1H), 5.09 (bt, J=ca. 10 Hz, 1H), 5.43 (dd, J=4.4 & 10.5 Hz, 1H), 7.5–7.9(br, 2H)

Example 28

Synthesis of Compound 28 and Compound 33

392 mg of Compound f obtained in REFERENCE EXAMPLE 6 was dissolved in 30 ml of anhydrous tetrahydrofuran. While adding a suspension of the sodium salt prepared from 239 mg of ethyl p-nitrobenzoylacetate and 50.0 mg of sodium hydride (60% content, oil dispersion) in 10 ml of tetrahydrofuran in several portions, the solution was stirred at ambient temperature for an hour and 50 minutes.

The reaction mixture was diluted with a phosphate buffer (pH 4) followed by extracting with chloroform. After washing with saturated aqueous sodium chloride solution, the organic layer was dried over anhydrous sodium sulfate and the desiccant was removed by filtration. The solvent was then distilled off. The residue obtained was purified by column chromatography (silica gel; chloroform:methanol=30:1) to give violet and yellow fractions, respectively. After the solvent was distilled off from these fractions, n-hexane-chloroform was added to give a power. The solvent was distilled off and the residue was thoroughly dried in vacuo to give 45.7 mg (yield, 8%) of Compound 33 as a violet powder.

The yellow fraction (20 mg) was dissolved in 5 ml of methanol and 200 mg of silica gel was added to the solution followed by refluxing for 4 hours and 10 minutes with stirring. The reaction mixture was treated as described above to give 10.2 mg (yield, 12%) of Compound 28 as a reddish violet powder. Compound 28 was obtained as the mixture of diastereoisomers associated with the side chain of the 6-position methyl and the proportion was approximately 1:1 by $^1$H-NMR.

Compound 33

TLC: R$_f$=0.64 (chloroform:methanol=9:1 ) FAB-MS (m/z): 569 (M$^+$+3); C$_{27}$H$_{26}$N$_4$O$_{10}$=566 IR (cm$^{-1}$):3400, 3340, 2900, 1760, 1740, 1690, 1660, 1610, 1550, 1380, 1240, 1090 $^1$H-NMR (270 MHz, chloroform-d$_1$) δ(ppm):1.07 (t, J=7.2 Hz, 3H), 2.28 (s, 3H), 2.2–2.4 (2H, overlapped with the peak of 1aN-methyl), 3.22 (s, 3H), 3.33 (d, J=21.1 Hz, 1H), 3.42 (d, J=21.1

Hz, 1H), 3.47 (dd, J=1.7 and 12.6 Hz, 1H), 3.65 (dd, J=4.7 & 10.6 Hz, 1H), 4.06 (d, J=ca. 13 Hz, 1H, overlapped with the peak of ethyl), 4.07 (q, J=7.2 Hz, 2H), 4.40 (t, J=10.6 Hz, 1H), 4.70 (dd, J=4.7 & 10.6 Hz, 1H), 4.72 (bs, 2H), 7.59 (d, J=8.9 Hz, 2H), 8.25 (d, J=8.9 Hz, 2H)

Compound 28

TLC: $R_f$=0.64 (chloroform:methanol=9:1) FAB-MS (m/z): 601 (M$^+$+3); $C_{28}H_{30}N_4O_{11}$=598 IR (cm$^{-1}$): 3400, 3350, 2900, 1760, 1740, 1660, 1560, 1480, 1370, 320, 1250, 1100 $^1$H-NMR (270 MHz, chloroform-d$_1$) δ(ppm): 1.13 and 1.14 (t, J=6.9 Hz, 3H), 2.27 and 2.28 (s, 3H), 2.2–2.3 (2H, overlapped with the peak of 1aN-methyl), 2.94 and 2.98 (dd, J=5.9 & 13.9 Hz, 1H), 3.2–3.3 (m, 1H, 6-CH$_2$ overlapped with the peak of 9a-methoxy), 3.18 and 3.20 (s, 3H), 3.43 (dd, J=1.7 & 12.5 Hz, 1H), 3.55 and 3.57 (dd, J=4.5 & 10.9 Hz, 1H), 4.00 (d, J=12.5 Hz, 1H), 4.09 (s, 3H), 4.0–4.2 (m, 2H), 4.33 and 4.34 (t, J=10.6 Hz, 1H), 4.49–4.57 (m, 1H), 4.70 (dd, J=4.5 & 10.4 Hz, 1H), 4.76 (bs, 2H), 8.12 and 8.13 (d, J=8.9 Hz, 2H), 8.31 (d, J=8.9 Hz, 2H)

Example 29

Synthesis of Compound 29

405 mg of Compound f obtained in REFERENCE EXAMPLE 6 was dissolved in 30 ml of anhydrous tetrahydrofuran. While adding a suspension of the sodium salt prepared from 110 μl of acetylacetone and 52.5 mg of sodium hydride (60% content, oil dispersion) in 10 ml of tetrahydrofuran in several portions, the solution was stirred at ambient temperature for 30 minutes.

The reaction mixture was subjected to work-up as in EXAMPLE 28. The residue obtained was purified by column chromatography (silica gel; chloroform:methanol=50:1) to give a violet fraction containing the desired product. After the solvent was distilled off from this fraction, n-hexane-chloroform was added to give a powder. The solvent was distilled off and the residue was thoroughly dried in vacuo to give 31.8 mg (yield, 6%) of Compound 29 as a violet powder.

TLC: $R_f$=0.38 (chloroform:methanol=9:1) FAB-MS (m/z): 430 (M$^+$+1), 432 (M$^+$+3); $C_{21}H_{23}N_3O_7$=429 IR (cm$^{-1}$): 3450, 3350, 2950, 2920, 1730, 1710, 1690, 1660, 1630, 1570, 1450, 1350, 1320, 1200, 1190, 1080 $^1$H-NMR (270MHz, chloroform-d$_1$) δ(ppm): 2.27 (s, 3H), 2.30 (s, 3H), 2.32 (s, 3H), 2.2–2.4(m, 2H), 3.20 (s, 3H), 3.0–3.3 (m, 2H), 3.45 (dd, J=2.0 & 12.9 Hz, 1H), 3.64 (dd, J=4.7 & 10.6 Hz, 1H), 4.04 (d, J=12.9 Hz, 1H), 4.40 (t, J=10.6 Hz, 1H), 4.70 (dd, J=4.7 & 10.6 Hz, 1H), 4.72 (bs, 2H)

Example 30

Synthesis of Compound 30

463 mg of Compound e obtained in REFERENCE EXAMPLE 5 was dissolved in 30 ml of anhydrous tetrahydrofuran. While adding a suspension of the sodium salt prepared from 152 mg of benzoylacetone and 48.4 mg of sodium hydride (60% content, oil dispersion) in 10 ml of tetrahydrofuran in several portions, the solution was stirred at ambient temperature for 15 minutes.

The reaction mixture was subjected to work-up as in EXAMPLE 28. The residue obtained was purified by column chromatography (silica gel; chloroform:methanol=40:1 to 20:1) to give a violet fraction. After the solvent was distilled off from this fraction, n-hexane-chloroform was added to give a powder. The solvent was distilled off and the residue was thoroughly dried in vacuo to give 47.9 mg (yield, 7.7%) of 1aN-allyloxycarbonyl derivative of Compound 30 as a violet powder.

Subsequently product obtained above was dissolved in 2 ml of anhydrous tetrahydrofuran, and 70 μl of triethylammonium formate and 8.1 mg of tetrakis (triphenylphosphine) palladium (0) were added to the solution. The mixture was stirred at ambient temperature for 2 hours and 10 minutes under an argon atmosphere.

The reaction mixture was purified directly by column chromatography (silica gel; chloroform:methanol=20:1) to give a violet fraction. This fraction was then treated as described above to give 11.7 mg (yield, 69%) of Compound 30 as a violet powder.

TLC: $R_f$=0.37 (chloroform:methanol=9:1) FAB-MS (m/z): 479 (M$^+$+2); $C_{25}H_{23}N_3O_7$=477 IR (cm$^{-1}$): 3400, 3330, 3240, 2900, 1750, 1690, 1660, 1600, 1480, 1390, 1360, 1240, 1230, 1220, 1190, 1100 $^1$H-NMR (270 MHz, chloroform-d$_1$) δ(ppm): 0.66 (bs, 1H), 1.87 (s, 3H), 2.85 (bs, 1H), 2.93 (bd, J=4.0 Hz, 1H), 3.15 (d, J=20.3 Hz, 1H), 3.24 (s, 3H), 3.27 (d, J=20.3 Hz, 1H), 3.49 (dd, J=1.8 & 12.8 Hz, 1H), 3.69 (dd, J=4.7 & 10.2 Hz, 1H), 4.07 (d, J=12.8 Hz, 1H), 4.61 (t, J=10.6 Hz, 1H), 4.7–4.8 (br, 2H), 4.73 (dd, J=4.7 & 10.7 Hz, 1H), 7.44–7.51 (m, 2H), 7.55–7.62(m, 1H), 7.78–7.83 (m, 2H)

Example 31

Synthesis of Compound 31

400 mg of Compound f obtained in REFERENCE EXAMPLE 6 was dissolved in 30 ml of anhydrous tetrahydrofuran. While adding a suspension of the sodium salt prepared from 150 μl of benzoylacetone and 48.9 mg of sodium hydride (60% content, oil dispersion) in 10ml of tetrahydrofuran in several portions, the solution was stirred at ambient temperature for an hour.

The reaction mixture was subjected to work-up as in EXAMPLE 28. The residue obtained was purified by column chromatography (silica gel; chloroform:methanol=30:1) to give a violet fraction. After the solvent was distilled off from this fraction, n-hexane-chloroform was added to give a powder. The solvent was distilled off and the residue was thoroughly dried in vacuoto give 88.7 mg (yield, 18%) of Compound 31 as a violet powder.

TLC: $R_f$=0.57 (chloroform:methanol=9:1) FAB-MS (m/z): 492 (M$^+$+1), 494 (M$^+$+3); $C_{26}H_{25}N_3O_7$=491 IR (cm$^{-1}$): 3400, 3300, 2880, 1760, 1740, 1690, 1660, 1610, 1480, 1390, 1360, 1240, 1190, 1110, 1040 $^1$H-NMR (270 MHz, chloroform-d$_1$) δ(ppm):1.87 (s, 3H), 2.28 (s, 3H), 2.2–2.4 (m, 2H), 3.21 (s, 3H), 3.1–3.3 (2H, 9a-overlapped with 9a methoxy), 3.44 (dd, J=1.7 & 12.8 Hz, 1H), 3.66 (dd, J=4.7 & 10.7 Hz, 1H),4.04 (d, J=12.8 Hz, 1H), 4.42 (t, J=10.7 Hz, 1H), 4.72 (dd, J=4.7 & 10.7 Hz, 1H), 4.78 (bs, 2H), 7.44–7.53 (m, 2H), 7.55–7.62 (m, 1H), 7.78–7.83(m, 2H)

Example 32

Synthesis of Compound 32

405 mg of Compound f obtained in REFERENCE EXAMPLE 6 was dissolved in 30 ml of anhydrous tetrahydrofuran. While adding a suspension of the sodium salt prepared from 130 μl of ethyl acetoacetate and 51.5 mg of sodium hydride (60% content, oil dispersion) in 10 ml of tetrahydrofuran in several portions, the solution was stirred at ambient temperature for 50 minutes.

The reaction mixture was subjected to work-up as in EXAMPLE 28. The residue obtained was purified by column chromatography (silica gel; chloroform:methanol=100:1)to give a violet fraction. After the solvent was distilled off from this fraction, n-hexane-chloroform was added to give a powder. The solvent was distilled off and the residue was thoroughly dried in vacuo to give 59.9 mg (yield, 13%) of Compound 32 as a violet powder.

TLC: $R_f=0.34$ (chloroform:acetonitrile:n-hexane=5:5:1 ) FAB-MS (m/z): 460 $(M^++1)$; $C_{22}H_{25}N_3O_8=459$ IR (cm$^{-1}$): 3450, 3350, 2950, 1720, 1710, 1700, 1640, 1630, 1580, 1570, 1450, 1360, 1330, 1310, 1210, 1190, 1090 $^1$H-NMR (270 MHz, chloroform -d$_1$) δ(ppm):1.32 (t, J=6.9 Hz, 3H), 2.27 (s, 3H), 2.20–2.35 (m, 2H), 2.39(s, 3H), 3.08 (d, J=20.4 Hz, 1H), 3.20 (d, J=20.4 Hz, 1H), 3.20 (s, 3H), 3.45 (dd, J=2.0 & 12.9 Hz, 1H), 3.63 (dd, J=4.6 & 10.9 Hz, 1H), 4.04 (d, J=12.9 Hz, 1H), 4.23 (q, 2H), 4.41 (bt, J=10.7 Hz, 1H), 4.70 (dd, J=4.6 & 10.6 Hz, 1H), 4.76 (bs, 2H)

Example 33

Synthesis of Compound 34

1.00 g of Compound c obtained in REFERENCE EXAMPLE 3 was dissolved in 50 ml of anhydrous tetrahydrofuran and 0.20 ml of anhydrous triethylamine and 372 mg of dimedone were added to the solution followed by stirring at ambient temperature for 2 hours and 15 minutes.

The reaction mixture was subjected to work-up as in EXAMPLE 28. The residue obtained was purified by column chromatography (silica gel; chloroform:methanol=30:1) to give a violet fraction.

After the solvent was distilled off from this fraction, n-hexane-chloroform was added to give a powder. The solvent was distilled off and the residue was thoroughly dried in vacuo to give 276.5 mg (yield, 31% based on 7-demethoxy-7-ethylenedioxy-6, 7-dihydro-6-phenyl-selenomitomycin B) of Compound 34 as a violet powder.

TLC: $R_f=0.32$ (chloroform:methanol=9:1 ) FAB-MS (m/z): 458 $(M^++3)$: $C_{23}H_{25}N_3O_7=455$ IR (cm$^{-1}$): 3470, 3420, 3300, 2950, 1710, 1660, 1630, 1590, 1390, 1350, 1340, 1200, 1190, 1110 $^1$H-NMR (270 MHz, pyridine-d$_5$) δ(ppm): 0.93 (s, 3H), 0.96 (s, 3H), 2.17 (s, 3H), 2.2–2.4 (m, 5H), 2.50 (d, J=4.6 Hz, 1H), 3.01 (d, J=20.5 Hz, 1H), 3.10 (d, J=20.5 Hz, 1H), 3.57 (dd, J=1.7 & 12.7 Hz, 1H), 4.13 (d, J=12.7 Hz, 1H), 4.26 (dd, J=3.3 & 9.1 Hz, 1H), 5.25 (dd, J=9.1 & 10.7 Hz, 1H), 5.43 (dd, J=3.3 & 10.7 Hz, 1H), 7.3–7.7 (br, 2H), 8.34 (br, 1H)

Example 34

Synthesis of Compound 35

732 mg of Compound c obtained in REFERENCE EXAMPLE 3 was dissolved in 50 ml of anhydrous tetrahydrofuran and 0.20 ml of anhydrous triethylamine and 218 mg of 1,3-cyclohexanedione were added to the solution followed by stirring at ambient temperature for 45 minutes.

The reaction mixture was subjected to work-up as in EXAMPLE 28. The residue obtained was purified by column chromatography (silica gel; chloroform:methanol=50:1 to 30:1) to give a violet fraction. After the solvent was distilled off from this fraction, n-hexane-chloroform was added to give a powder. The solvent was distilled off and the residue was thoroughly dried in vacuo to give 151.4 mg (yield, 25% based on 7-demethoxy-7-ethylenedioxy-6, 7-dihydro-6-phenyl-selenomitomycin B) of Compound 35 as a violet powder.

TLC: $R_f=0.35$ (chloroform:methanol=9:1) FAB-MS (m/z): 429 $(M_++2)$, 430 $(M_++3)$; $C_{21}H_{21}N_3O_7=427$ IR (cm$^{-1}$):3450, 3200, 2950, 1710, 1660, 1620, 1570, 1450, 1380, 1350, 1210, 1190, 1120, 1070, 1060 $^1$H-NMR (270 MHz, chloroform-d$_1$) δ(ppm): 2.05 (m, 2H), 2.26 (s, 3H), 2.28 (s, 2H), 2.45 (m, 2H), 2.61 (m, 2H), 2.95(d, J=20.8 Hz, 1H), 3.08 (d, J=20.8 Hz, 1H), 3.45 (d, J=12.9 Hz, 1H), 3.76 (t, J=4.1 Hz, 1H), 4.00 (d, J=12.9 Hz, 1H), 4.62 (bs, 1H), 4.72 (d, J=4.1 Hz, 2H), 4.76 (bs, 2H)

Example 35

Synthesis of Compound 36 and Compound 37

After 568 mg of Compound e obtained in REFERENCE EXAMPLE 5 was dissolved in 40 ml of anhydrous tetrahydrofuran, 0.20 ml of anhydrous triethylamine and 157 mg of 5-methyl-1, 3-cyclohexanedione were added to the solution. The mixture was stirred at ambient temperature for an hour and 15 minutes.

The reaction mixture was subjected to work-up as in EXAMPLE 28. The residue obtained was again dissolved in 100 ml of chloroform. 100 ml of silica gel was added to the solution to adsorb the product and allowed to stand at ambient temperature for 20 hours and 30 minutes.

The silica gel was eluted with an eluent (chloroform:methanol =9:1 ). The resulting violet solution was concentrated under reduced pressure and the residue was purified by column chromatography (silica gel; chloroform:methanol=50:1) to give a violet fraction. After the solvent was distilled off from this fraction, n-hexane-chloroform was added to give a powder. The solvent was distilled off and the residue was thoroughly dried in vacuo to give 405.1 mg (yield, 62%) of the 1aN-allyloxycarbonyl derivatives of Compounds 36 and 37 as a violet powder.

Subsequently, 405.0 mg of the product obtained above was

Subsequently, 405.0 mg of the product obtained above was dissolved in 20 ml of anhydrous tetrahydrofuran, and 0.40 ml of triethylammonium formate and 42 mg of tetrakis (triphenylphosphine) palladium (0)was added to the solution. The mixture was stirred at ambient temperature for 35 minutes under an argon atmosphere.

The reaction mixture was purified directly by column chromatography (silica gel; chloroform:methanol=50:1 to 20:1)to give a violet fraction. This fraction was then treated as described above to give 222.9 mg (yield, 66%) of the mixture of Compounds 36 and 37 as a violet powder. Each diastereoisomer was isolated and purified by preparative HPLC to give 100.5 mg of a diastereoisomer (Compound 36) having a shorter retention time and 74.3 mg of another diastereoisomer (Compound 37) having a longer retention time.

Compound 36

TLC: $R_f=0.37$ (chloroform:methanol 9:1) HPLC: $t_R$ =20.83 minutes (eluent: acetonitrile:water=25:75 column: YMC AM-312 S-5; flow rate: 1.0 ml/min) FAB-MS (m/z): 442$(M^++1)$; $C_{22}H_{23}N_3O_7=441$ IR(cm$^{-1}$): 3450, 3350, 3300, 3200, 2960, 2890, 1720, 1660, 1630, 1570, 1450, 1390, 1340, 1200, 1190, 1160, 1130, 1070, 1030 $^1$H-NMR (270 MHz, chloroform-$d_1$) δ(ppm): 0.5–1.0 (br, 1H), 1.11 (d, J=5.9 Hz, 3H), 2.13 (dd, J=12.1 & 16.0 Hz, 1H), 2.2–2.4 (m, 2H), 2.54 (dd, J=2.5 & 16.0 Hz, 1H), 2.66 (m, 1H), 2.85 (bd, J=4.5 Hz, 1H), 2.92(d, J=4.5 Hz, 1H), 2.94(d, J=20.8 Hz, 1H), 3.12 (d, J=20.8 Hz, 1H), 3.22(s, 3H), 3.49 (dd, J=1.5 & 12.9 Hz, 1H), 3.67 (dd, J=4.6 & 10.4 Hz, 1H), 4.07 (d, J=12.9 Hz, 1H), 4.58 (bt, J=10.6 Hz, 1H), 4.72 (dd, j=4.7 & 10.6 Hz, 1H), 4.77 (bs, 2H)

Compound 37

TLC: $R_f$=0.37 (chloroform:methanol=9:1) HPLC: $t_R$ =22.60 minutes (eluent: acetonitrile:water=25:75 column:
YMC AM-312 S-5; flow rate: 1.0 ml/min) FAB-MS (m/z): 442 (M++1); $C_{22}H_{23}N_3O_7$=441 IR (cm$^{-1}$): 3450, 3350, 3300, 3200, 2960, 2890, 1720, 1660, 1630, 1570, 1450, 1390, 1340, 1200, 1190, 1160, 1130, 1070, 1030 $^1$H-NMR (270 MHz, chloroform-$d_1$) δ(ppm): 0.5–1.0 (br, 1H), 1.12(d, J=5.9 Hz, 3H), 2.14 (dd, J=12.4 & 15.8 Hz, 1H), 2.2–2.4 (m, 2H), 2.54 (dd, J=2.0 & 15.8 M, 1H), 2.66(m, 1H), 2.85 (dd, J=2.0 & 4.5 Hz, 1H), 2.92 (d, J=4.5 Hz, 1H), 2.99 (d, J=20.8 Hz, 1H), 3.08(d, J=20.8 Hz, 1H), 3.22 (s, 3H), 3.49 (dd, J=1.5 & 12.9 Hz, 1H), 3.67 (dd, J=4.7 & 10.1 Hz, 1H), 4.07 (d, J=12.9 Hz, 1H), 4.58 (bt, J=10.4 Hz, 1H), 4.71 (dd, J=4.7 & 10.6 Hz, 1H), 4.7–4.8 (bs, 2H)

Example 36

Synthesis of Compound 38 and Compound 39

After 928 mg of Compound e obtained in REFERENCE EXAMPLE 5 was dissolved in 70 ml of dichloromethane, 0.20 ml of anhydrous triethylamine and 437 mg of 5-(p-methoxyphenyl)-1,3-cyclohexanedione were added to the solution. The mixture was stirred at ambient temperature for 50 minutes.

The reaction mixture was subjected to work-up as in EXAMPLE 28. The residue obtained was again dissolved in 200 ml of chloroform. 100 ml of silica gel was added to the solution to adsorb the product and allowed to stand at ambient temperature for 17 hours.

The silica gel was eluted with an eluent (chloroform:methanol =9:1 ). The resulting violet solution was concentrated under reduced pressure and the residue was purified by column chromatography (silica gel; chloroform:methanol=100:1) to give a violet fraction. After the solvent was distilled off from this fraction, n-hexane-chloroform was added to give a powder. The solvent was distilled off and the residue was thoroughly dried in vacuo to give 923.4 mg (yield, 73%) of the 1aN-allyloxycarbonyl derivatives of Compounds 38 and 39 as a violet powder.

Subsequently, 802.5 mg of the product obtained above was dissolved in 40 ml of anhydrous tetrahydrofuran, and 1.0 ml of triethylammonium formate and 43 mg of tetrakis (triphenylphosphine) palladium (0) were added to the solution. The mixture was stirred at ambient temperature for 25 minutes under an argon atmosphere.

The reaction mixture was purified directly by column chromatography (silica gel; chloroform:methanol=50:1 to 20:1) to give a violet fraction. This fraction was then treated as described above to give 126.6 mg (yield, 19%) of the mixture of Compounds 38 and 39 as a violet powder. Each diastereoisomer was isolated and purified by preparative HPLC to give 44.5 mg of a diastereoisomer (Compound 38) having a shorter retention time and 34.2 mg of another diastereoisomer (Compound 39) having a longer retention time.

Compound 38

TLC: $R_f$=0.38 (chloroform:methanol=9:1) HPLC: $t_R$ =9.66 minutes (eluent: acetonitrile:water=40:60; column:
YMC AM-312 S-5; flow rate: 1.0 ml/min) FAB-MS (m/z): 534 (M++1); $C_{28}H_{27}N_3O_8$=533 IR (cm$^{-1}$):3500, 3400, 3300, 3180, 2920, 1720, 1660, 1630, 1580, 1510, 1390, 1340, 1250, 1200, 1160, 1120, 1070, 1030 $^1$H-NMR (270MHz, chloroform-$d_1$) δ(ppm): 0.8.–1.0 (br, 1H), 2.61 (dd, J=12.4 & 16.3 Hz, 1H), 2.7–3.0 (m, 4H), 2.93 (d, J=4.5 Hz, 1H), 2.99 (d, J=20.3 Hz, 1H), 3.17 (d, J=20.3 Hz, 1H), 3.22 (s, 3H), 3.3–3.4(m, 1H), 3.50 (dd, J=2.0 & 12.9 Hz, 1H), 3.67 (dd, J=4.6 & 10.1 Hz, 1H), 3.80 (s, 3H), 4.08 (d, J=12.9 Hz, 1H), 4.59 (bt, J=10.4 Hz, 1H), 4.72 (dd, J=4.6 & 10.9 Hz, 1H), 4.7–4.8 (br, 2H), 6.88 (d, J=8.4 Hz, 2H), 7.15 (d, J=8.4 Hz, 2H)

Compound 39

TLC: $R_f$=0.38 (chloroform:methanol=9:1) HPLC: $t_R$ =10.40 minutes (eluent: acetonitrile:water=40:60; column: YMC AM-312 S-5; flow rate: 1.0 ml/min) FAB-MS (m/z): 534 (M++1); $C_{28}H_{27}N_3O_8$=533 IR (cm$^{-1}$):3500, 3400, 3300, 3180, 2920, 1720, 1660, 1650, 1630, 1580, 1570, 1520, 1390, 1340, 1250, 1200, 1070, 1030 $^1$H-NMR (270 MHz, chloroform-$d_1$) δ(ppm): 0.8–1.0 (br, 1H), 2.62 (dd, J=12.4 & 16.1 Hz, 1H), 2.77 (dd, J=4.5 & 16.1 Hz, 1H), 2.7–2.9 (m, 3H), 2.92 (d, J=5.0 Hz, 1H), 3.04 (d, J=20.3 Hz, 1H), 3.13 (d, 20.3 Hz, 1H), 3.23 (s, 3H), 3.3–3.4 (m, 1H), 3.50 (dd, J=2.0 & 12.9 Hz, 1H), 3.68 (dd, J=4.8 & 10.4 Hz, 1H), 3.81 (s, 3H), 4.08 (d, J=12.9 Hz, 1H), 4.59 (bt, J=10.4 Hz, 1H), 4.71 (dd, J=4.8 & 10.6 Hz, 1H), 4.7–4.8 (br, 2H), 6.88 (d, J=8.4 Hz, 2H), 7.15(d, J=8.4 Hz, 2H)

Example 37

Synthesis of Compound 40

After 932 mg of Compound e obtained in REFERENCE EXAMPLE 5 was dissolved in 70 ml of dichloromethane, 0.20 ml of anhydrous triethylamine and 520 mg of 5-(2,6-dichlorophenyl)-1,3-cyclohexanedione were added to the solution. The mixture was stirred at ambient temperature for 40 minutes.

The reaction mixture was subjected to work-up as in EXAMPLE 28. The residue obtained was again dissolved in 200 ml of chloroform. 100 ml of silica gel was added to the solution to adsorb the product and allowed to stand at ambient temperature for 21 hours.

The silica gel was eluted with an eluent (chloroform:methanol =9:1 ). The resulting violet solution was concentrated under reduced pressure and the residue was purified by column chromatography (silica gel; chloroform:methanol=100:1) to give a violet fraction. After the solvent was distilled off from this fraction, n-hexane-chloroform was added to give a powder. The solvent was distilled off and the residue was thoroughly dried in vacuo to give 601.0 mg (yield, 47%) of the 1aN-allyloxycarbonyl derivative of Compound 40 as a violet powder.

Subsequently, 591.5 mg of the product obtained above was dissolved in 30 ml of anhydrous tetrahydrofuran, and 0.50 ml of triethylammonium formate and 31 mg of tetrakis (triphenylphosphine) palladium (0) were added to the solution. The mixture was stirred at ambient temperature for 23 minutes under an argon atmosphere.

The reaction mixture was purified directly by column chromatography (silica gel; chloroform:methanol=20:1) to give a violet fraction. This fraction was then treated as described above to give 35.3 mg (yield, 7%) of Compound 40 as a violet powder.

TLC: $R_f$=0.49 (chloroform:methanol=9:1) FAB-MS(m/z): 571,573,575 (M+ +1); $C_{27}H_{23}{}^{35}Cl_2N_3O_7$=570 IR (cm$^{-1}$): 2500, 3400, 3300, 3200, 2920, 1720, 1640, 1630, 1580, 1570, 1440, 1390, 1340, 1200, 1080 $^1$H-NMR (270 MHz, chloroform -d$_1$) δ(ppm): 0.8–0.9 (br, 1H), 2.52 (dd, J=4.2 & 17.1 Hz, 1H), 2.66 (dd, J=4.2 & 17.1 Hz, 1H), 2.86 (dd, J=2.0 & 4.5 Hz, 1H), 2.93 (d, J=4.5 Hz, 1H), 3.08 (bd, J=16.8 Hz, 1H), 3.14 (bd, J=16.Hz, 1H), 3.23(s, 3H), 3.51 (dd, J=2.0 & 12.9 Hz, 1H), 3.45–3.71(m, H), 3.68 (dd, J=4.5 & 10.4 Hz, 1H), 4.09 (d, J=12.9 Hz, 1H), 4.3–4.5(m, H), 4.59 (t, J=10.6 Hz, 1H), 4.71 (dd, J=4.5 & 10.9 Hz, 1H), 4.7–4.8 (br, H), 7.16 (t, J=8.2 Hz, 1H), 7.33 (m, 2H)

Hereafter the structures of the Compounds in REFERENCE EXAMPLES are given.

TABLE 6

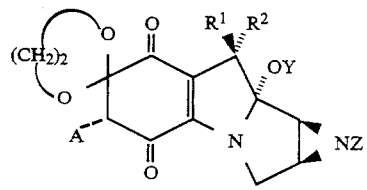

| Compound | A | $R^1$ | $R^2$ | Y | Z |
|---|---|---|---|---|---|
| a | =CH$_2$ | CH$_2$OCONH$_2$ | H | CH$_3$ | COCH$_3$ |
| b | —SePh | CH$_2$OCONH$_2$ | H | CH$_3$ | COCH$_3$ |
| c | =CH$_2$ | H | CH$_2$OCONH$_2$ | H | CH$_3$ |
| d | { —SePh / —CH$_3$ | CH$_2$OCONH$_2$ | H | CH$_3$ | CO$_2$CH$_2$CH=CH$_2$ |
| e | =CH$_2$ | CH$_2$OCONH$_2$ | H | CH$_3$ | CO$_2$CH$_2$CH=CH$_2$ |
| f | =CH$_2$ | CH$_2$OCONH$_2$ | H | CH$_3$ | CH$_3$ |

*SePh represents phenylseleno.

REFERENCE EXAMPLE 1

Synthesis of 1a-acetyl-7-demethoxy-6-demethyl-7-ethylenedioxy-6, 7-dihydro-6-methylenemitomycin A (Compound a)

After 5.77 g of 1a-acetyl-7-demethoxy-7-ethylenedioxy-6, 7-dihydro-6-phenylselenomitomycin A (described in JP-A 70490/89) was dissolved in 100 ml of dichloromethane, 2.82 g of potassium carbonate was added to the solution. Then a solution of 2.59 g of m-chloroperbenzoic acid (purity about 80%) in 50 ml of dichloromethane was added dropwise to the solution at −40° C. over 15 minutes. Subsequently the mixture was stirred at −40 ° to −30° C. for 40 minutes and then at 20° C. for further 50 minutes. The reaction mixture was washed with a mixture (1:1) of aqueous sodium thiosulfate solution (M/10) and saturated aqueous sodium hydrogencarbonate solution and further with saturated aqueous sodium chloride solution. After drying over anhydrous sodium sulfate, the mixture was concentrated under reduced pressure. n-Hexane was added to the residue to give a powder. The obtained powder was filtered and thoroughly dried in vacuo to give 3.77 g (yield, 90%) of Compound a. The purity of Compound a was about 90% by $^1$H-NMR.

TLC: $R_f$=0.42 (chloroform:acetonitrile:n-hexane=5:5:1) FAB-MS (m/z): 420 (M+ +1); $C_{19}H_{21}N_3O_8$=419 $^1$H-NMR (400 MHz, chloroform-d$_1$/pyridine-d$_5$) δ(ppm): 2.08 (s, 3H), 3.17 (s, 3H), 3.24 (dd, J=4.4 & 2.0 Hz, 1H), 3.50(d, J=4.4 Hz, 1H), 3.48 (dd, J=13.3 & 2.0 Hz, 1H), 3.79 (dd, J=11.1 & 4.9 Hz, 1H), 4.17 (t, J=10.8 Hz, 1H), 4.04–4.29(m, 4H), 4.38(d, J=13.3 Hz, 1H), 5.04(dd, J=10.8 & 4.7 Hz, 1H), 5.79 (bs, 2H), 6.09 (bs, 1H), 6.36 (bs, 1H)

REFERENCE EXAMPLE 2

Synthesis of 1a-acetyl-7-demethoxy-6-demethyl-7-ethylenedioxy-6, 7-dihydro-6-phenylselenomitomycin A (Compound b)

After 421 mg of Compound a obtained in REFERENCE EXAMPLE 1 was dissolved in 25 ml of anhydrous tetrahydrofuran, 238 mg of N-(phenylselenenyl) morphotine was added to the solution. The mixture was stirred at 25° C. for 3 hours. The reaction mixture was purified directly by column chromatography (silica gel; chloroform: methanol=30:1) to give a yellow fraction. The solvent was distilled off from this fraction and the residue was dissolved in a small amount of chloroform. n-Hexane was added to give a powder. The powder was filtered and thoroughly dried in vacuo to give 318 mg (yield, 56%) of Compound b as a yellow powder. Compound b was the equilibrium mixture of diastereoisomer based on the configuration at the 6-position.

TLC: $R_f$=0.30 (chloroform-acetonitrile-n-hexane=5:5:1) FAB-MS (m/z): 562, 564 (M+ +1); $C_{24}H_{25}N_3O_8{}^{78}Se$=561 H-NMR (400 MHz, chloroform-d$_1$) δ(ppm): major diastereoisomer: 2.20 (s, 3H), 3.21 (s, 3H), 3.26 (dd, J=2.0 & 4.7 Hz, 1H), 3.41 (dd, J=2.0 & 13.0 Hz, 1H), 3.52 (d, J=4.7 Hz, 1H), 3.73 (dd, =4.9 & 10.8 Hz, 1H), 3.84 (d, J=13.0 Hz, 1H), 4.02 (s, 1H), 4.19 (t, J=11 Hz, 1H), 4.01–4.20 (m, 3H), 4.41 (m, 1H), 4.91 (bs, 2H), 4.95 (dd, J=4.9 & 11.1 Hz, 1H), 7.28–7.38 (m, 3H), 7.61 (m, 2H) minor diastereoisomer: 2.10 (s, 3H), 3.21 (s, 3H), 3.23 (dd, J=2.0 & 4.4 Hz, 1H), 3.39 (dd, J=2.0 & 13.0 Hz, 1H), 3.48 (d, J=4.4 Hz, 1H), 3.67 (dd, J=4.7 & 10.8 Hz, 1H), 4.17 (s, 1H), 4.01–4.20 (m, 4H), 4.31 (m, 1H), 4.40 (d, J=13.0 Hz. 1H), 4.8t (dd, J=4.7 & 10.8 Hz, 1H), 4.89 (bs, 2H), 7.28–7.38 (m, 3H), 7.61 (m, 2H)

REFERENCE EXAMPLE 3

Synthesis of 7-demethoxy-6-demethyl-7-ethylenedioxy-6, 7-dihydro-6-methylenemitomycin B (Compound c)

After 1.25 g of 7-demethoxy-7-ethylenedioxy-6, 7-dihydro-6-phenylselenomitomycin A (described in JP-A 70490/89) was dissolved in 25 ml of dichloromethane, 650 mg of potassium carbonate was added to the solution. Then a solution of 630 mg of m-chloroperbenzoic acid (purity about 80%) in 15 ml of dichloromethane was added dropwise to the solution at −40° C. over 15 minutes. Subsequently the mixture was stirred at −30° C. for 35 minutes and then at 20° C. for further 40 minutes. The reaction mixture was filtered through filter aide (dialomucous earth). After the filtrate was concentrated under reduced pressure, n-hexane was added to the residue to give a powder. The powder was filtered and thoroughly dried in vacuo to give 1.05 g of the crude product of Compound c as a yellow powder.

TLC: $R_f=0.30$ (chloroform:methanol=9:1)

REFERENCE EXAMPLE 4

Synthesis of la-allyloxycarbonyl-7-demethoxy-7-ethylenedioxy-6, 7-dihydro-6-phenylselenomitomycin A (Compound d)

After 1.31 g of la-allyloxycarbonyl-7-demethoxy-7-ethylenedioxy-6, 7-dihydromitomycin A (described in JP-A 49786/90) was dissolved in 30 ml of anhydrous acetonitrile and 1.0 ml of triethylamine, a solution of 1.01 g of phenylselenenyl bromide in 10 ml of anhydrous acetonitrile was added dropwise to the solution at 0° C. over 5 minutes. The mixture was stirred at ambient temperature for 14 hours. The reaction mixture was diluted with a phosphate buffer (M/20, pH 7) followed by extraction with chloroform. The organic layer obtained was washed with saturated aqueous ammonium chloride solution and saturated aqueous sodium chloride solution successively. After drying over anhydrous sodium sulfate, the solvent was distilled off under reduced pressure. The residue was purified by column chromatography (silica gel; chloroform:methanol=100:1)to give a yellow fraction. The solvent was distilled off from this fraction and the residue was dissolved in a small amount of chloroform. n-Hexane was added to give a powder. The powder was filtered and thoroughly dried in vacuo to give 1.36 g (yield, 78%) of the desired compound as a yellow powder. The product was the mixture of diastereoisomers based on the configuration at the 6-position.

TLC: $R_f=0.54$ (chloroform:methanol=15:1) $^1$H-NMR (90 MHz, chloroform-d$_1$) δ(ppm): major diastereoisomer: (major peaks) 1.54 (s, 3H), 3.18 (s, 3H), 5.24 (dd, J=2 & 9 Hz, 1H), 5.31 (dd, J=2 & 18 Hz, 1H), 5.6–6.2 (m, 1H), 7.2–7.8 (m, 5H) minor diastereoisomer: (major peaks) 1.40 (s, 3H), 3.28 (s, 3H)

REFERENCE EXAMPLE 5

Synthesis of la-allyloxycarbonyl-7-demethoxy-6-demethyl-7-ethylenedioxy-6, 7-dihydro-6-methylenemitomycin A (Compound e)

After Compound d (3.89 g) obtained in REFERENCE EXAMPLE 4 was dissolved in 70 ml of dichloromethane, 2.62 g of potassium carbonate was added to the solution. Then a solution of 2.13 g of m-chloroperbenzoic acid (purity about 80%) in 40 ml of dichloromethane was added dropwise to the solution at −40° C. over 10 minutes. Subsequently the mixture was stirred at −40° C. for 30 minutes and then at 20° C. for further an hour. The reaction mixture was washed with a mixture (1:1) of aqueous sodium thiosulfate solution (M/10) and saturated aqueous sodium hydrogencarbonate solution and further with saturated aqueous sodium chloride solution. After drying over anhydrous sodium sulfate, the mixture was concentrated under reduced pressure. n-Hexane was added to the residue to give a powder. The obtained powder was filtered and thoroughly dried in vacuo to give 2.25 g (yield, 78%) of Compound e. The purity of Compound e was about 90% by $^1$H-NMR.

TLC: $R_f=0.66$ (chloroform:methanol=9:1) $^1$H-NMR (90 MHz, chloroform-d$_1$) δ(ppm): (major peaks) 3.22 (s, 3H), 5.26 (dd, J=2 & 11 Hz, 1H), 5.30 (dd, J=2 & 18 Hz, 1H), 6.11 (s, 1H), 6.38 (s, 1H)

REFERENCE EXAMPLE 6

Synthesis of 7-demethoxy-6-demethyl-7-ethylenedioxy-6, 7-dihydro-6-methylenemitomycin F (Compound f)

After 2.74 g of 7-demethoxy-7-ethylenedioxy-6, 7-dihydro-6-phenylselenomitomycin F (described in JP-A 167282/90) was dissolved in 100 ml of dichloromethane, 2.09 g of potassium carbonate was added to the solution. While stirring at −40° C., a solution of 1.39 g of m-chloroperbenzoic acid (purity about 80%) in 50 ml of dichloromethane was added dropwise to the solution over 15 minutes. Subsequently the mixture was stirred at −40° to −20° C. for 40 minutes and then at 20° C. for further an hour and 50 minutes.

The reaction mixture was washed with a mixture (1:1) of aqueous sodium thiosulfate solution (M/10) and saturated aqueous sodium hydrogencarbonate solution and further with saturated aqueous sodium chloride solution. After drying over anhydrous sodium sulfate, the mixture was concentrated under reduced pressure. n-Hexane was added to the residue to give a powder. The powder obtained was filtered and thoroughly dried in vacuo to give 1.73 g (yield, 89%) of Compound f. The purity of Compound f was about 90% by $^1$H-NMR.

TLC: $R_f=0.51$ (chloroform:methanol=9:1) FAB-MS:392 (M++1); $C_{18}H_{21}N_3O_7=391$ IR (cm$^{-1}$): 3450, 3370, 2960, 1720, 1660, 1570, 1450, 1400, 1360, 1340, 1210, 1140, 1120, 1060 $^1$H-NMR (400 MHz, chloroform-d$_1$)δ(ppm): 2.24 (dd, J=2.2 & 4.7 Hz, 1H), 2.26 (s, 3H), 2.30 (d, J=4.7 Hz, 1H), 3.19 (s, 3H), 3.44 (dd, J=2.2 & 12.6 Hz, 1H), 3.61 (dd, J=4.7 & 10.6 Hz, 1H), 4.15 (d, J=12.6 Hz, 1H), 4.06–4.34 (m, 4H), 4.40 (t, J=10.6 Hz, 1H), 4.73 (bs, 2H), 4.74 (dd, J=4.7 & 10.6 Hz, 1H), 6.07 (d, J=1.5 Hz, 1H), 6.34 (d, J=1.5 Hz, 1H)

According to the present invention, novel mitomycin derivatives having an excellent antitumor activity are provided.

what is claimed is:

1. A mitomycin derivative represented by the formula:

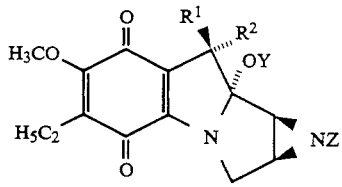

wherein Y and Z represent independently methyl or hydrogen; one of $R^1$ and $R^2$ represents $CH_2OCONH_2$ and the other represents hydrogen.

2. A pharmaceutical composition comprising a compound according to claim 1 as the active ingredient and pharmaceutically acceptable carrier.

* * * * *

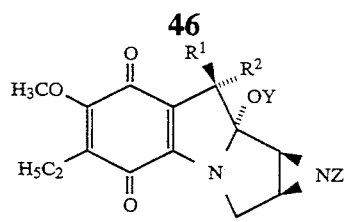

wherein Y and Z represent independently methyl or hydrogen; one of $R^1$ and $R^2$ represents $CH_2OCONH_2$ and the other represents hydrogen.

2. A pharmaceutical composition comprising a compound according to claim 1 as the active ingredient and pharmaceutically acceptable carrier.

* * * * *